US012758487B2

(12) United States Patent
Harlin et al.

(10) Patent No.: US 12,758,487 B2

(45) **Date of Patent: *Oct. 13, 2026**

(54) METHODS FOR DOSE INITIATION OF ARIPIPRAZOLE TREATMENTS

(71) Applicant: OTSUKA PHARMACEUTICAL CO., LTD., Tokyo (JP)

(72) Inventors: Matthew Harlin, Severna Park, MD (US); Xiaofeng Wang, Ellicott City, MD (US); Yanlin Wang, Jersey City, NJ (US); Arash Raoufinia, Mclean, VA (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/732,392

(22) Filed: Jun. 3, 2024

(65) Prior Publication Data

US 2024/0374506 A1 Nov. 14, 2024

Related U.S. Application Data

(63) Continuation of application No. 17/907,583, filed as application No. PCT/JP2021/014194 on Apr. 1, 2021, now abandoned.

(60) Provisional application No. 63/003,544, filed on Apr. 1, 2020.

(51) Int. Cl.
*A61K 9/00* (2006.01)
*A61K 31/496* (2006.01)
*A61P 25/18* (2006.01)

(52) U.S. Cl.
CPC .......... *A61K 9/0019* (2013.01); *A61K 9/0053* (2013.01); *A61K 31/496* (2013.01); *A61P 25/18* (2018.01)

(58) Field of Classification Search
CPC .. A61K 9/0019; A61K 9/0053; A61K 31/496; A61K 47/10; A61K 47/32; A61K 47/38; A61P 25/18; A61P 25/28
USPC .......................................................... 514/253
See application file for complete search history.

(56) References Cited

U.S. PATENT DOCUMENTS

| | | | |
|---|---|---|---|
| 7,807,680 B2 | 10/2010 | Kostanski et al. | |
| 8,030,313 B2 | 10/2011 | Kostanski et al. | |
| 8,338,427 B2 | 12/2012 | Brown | |
| 8,338,428 B2 | 12/2012 | Brown | |
| 8,399,469 B2 | 3/2013 | Bando et al. | |
| 8,722,679 B2 | 5/2014 | Kostanski et al. | |
| 8,759,351 B2 | 6/2014 | Brown | |
| 8,993,761 B2 | 3/2015 | Bando et al. | |
| 9,089,567 B2 | 7/2015 | Jordan et al. | |
| 10,525,057 B2 * | 1/2020 | Raoufinia | A61K 9/0019 |
| 10,980,803 B2 * | 4/2021 | Raoufinia | A61K 9/10 |
| 11,154,553 B1 * | 10/2021 | Raoufinia | A61K 9/0019 |
| 11,273,158 B2 * | 3/2022 | Von Moltke | A61K 31/496 |
| 11,400,087 B2 * | 8/2022 | Raoufinia | A61K 45/06 |
| 2015/0087654 A1 * | 3/2015 | Raoufinia | A61K 9/10 514/253.07 |
| 2019/0099494 A1 | 4/2019 | Kaneko et al. | |
| 2019/0298716 A1 * | 10/2019 | Von Moltke | A61K 47/26 |

FOREIGN PATENT DOCUMENTS

| | | |
|---|---|---|
| CN | 110327296 A | 10/2019 |
| EP | 3607940 A1 | 2/2020 |
| EP | 2234617 B1 | 3/2021 |
| WO | 2005041937 A2 | 5/2005 |
| WO | 2009001697 A2 | 12/2008 |
| WO | 2021201239 A1 | 10/2021 |

OTHER PUBLICATIONS

Jann et al. CNS Drugs (2018) 32:241-257, https://doi.org/10.1007/s40263-018-0508-6, "Long-Acting Injectable Second-Generation Antipsychotics: An Update and Comparison Between Agents". (Year: 2018).*

Raoufinia et al. Current Medical Research and Opinion, 2015, 31:3, 583-592, hereafter Raoufinia 2015 , DOI: 10.1185/03007995.2015.1006356, "Initiation of aripiprazole once-monthly in patients with schizophrenia" (Year: 2015).*

Wang et al. Current Medical Research and Opinion, 2021, 37:11, 1961-1972, DOI: 10.1080/03007995.2021. 1965974, An alternative start regimen with aripiprazole once-monthly in patients with schizophrenia: population pharmacokinetic analysis of a single-day, two-injection start with gluteal and/or delt (Year: 2021).*

Cameron et al. Current Medical Research and Opinion, 2018, 34:4, 725-733, DOI: 10.1080/03007995.2017.1410471 Efficacy and safety of aripiprazole lauroxil once monthly versus aripiprazole once-monthly long-acting injectable formulations in patients with acute symptoms of schizophrenia: an indirect (Year: 2018).*

Abilify Maintena™ Prescribing information (2013) (Year: 2013).*

Croxtall J.D. CNS Drugs 26, 155-183 (2012). https://doi.org/10.2165/11208400-000000000-00000, Aripiprazole : A Review of its Use in the Management of Schizophrenia in Adults (Year: 2012).*

Hard et al. Journal of Clinical Psychopharmacology 37(3), p. 289-295, Jun. 2017, DOI: 10.1097/JCP.0000000000000691, "Aripiprazole Lauroxil Pharmacokinetic Profile of This Long-Acting Injectable Antipsychotic in Persons With Schizophrenia". (Year: 2017).*

(Continued)

*Primary Examiner* — Jared Barsky
*Assistant Examiner* — Liyuan Mou
(74) *Attorney, Agent, or Firm* — Finnegan, Henderson, Farabow, Garrett & Dunner, LLP

(57) ABSTRACT

The present disclosure is directed to a method of dose initiation for an aripiprazole treatment to a patient in need thereof; the patient is administered two, separate 100 to 500 mg injections of an aripiprazole intramuscular (IM) depot formulation at separate gluteal and/or deltoid injection sites, and a single dose of oral aripiprazole. The administration occurs on a first day of the treatment.

10 Claims, 30 Drawing Sheets

(56) References Cited

OTHER PUBLICATIONS

Chue et al. Current Medical Research and Opinion, 2016,32:3, 441-452, DOI:10.1185/03007995.2015.1123145, A review of aripiprazole long-acting injection. (Year: 2016).*
NDA202971 Clinical Pharmacology review for Abilify Maintena , 202971Orig1s000ClinPharmR, retrieved from https://www.accessdata.fda.gov/drugsatfda_docs/nda/2013/202971Orig1s000ClinPharmR.pdf (Year: 2013).*
Abilify Maintena Summary of product characteristics updated on Dec. 30, 2020, retrieved from https://web.archive.org/web/20201230050758/https://www.ema.europa.eu/en/documents/product-information/abilify-maintena-epar-product-information_en.pdf. (Year: 2020).*
Mallikaarjun et al. Schizophr Res 2013;150:281-8, DOI: 10.1016/j.schres.2013.06.041, Pharmacokinetics, tolerability and safety of aripiprazole once-monthly in adult schizophrenia: an open-label parallel-arm, multiple-dose study. (Year: 2013).*
Fleischhacker et al. Aripiprazole once-monthly for treatment of schizophrenia: double-blind, randomised, non-inferiority study. The British Journal of Psychiatry , vol. 205 , Issue 2 , Aug. 2014 , pp. 135-144, DOI: https://doi.org/10.1192/bjp.bp.113.134213 (Year: 2014).*
Abilify Maintena® label 2025 , retrieved from https://www.accessdata.fda.gov/drugsatfda_docs/label/2025/202971s018,217006s001lbl.pdf (Year: 2025).*
Wang et al. Current Medical Research, 2021, vol. 37, No. 11, 1961-1972, doi: 10.1080/03007995.2021.1965974., An alternative start regimen with aripiprazole once-monthly in patients with schizophrenia (Year: 2021).*
Marjie L. Hard et al., “Pharmacokinetic Profile of a 2-Month Dose Regimen of Aripiprazole Lauroxil . . . ”, CNS Drugs, vol. 31, No. 7,Jun. 8, 2017, p. 617-624.
Leslie Citrome, “Aripiprazole long-acting injectable formulations for schizophrenia . . . ” Expert Review of Clinical Pharmacology Ltd., vol. 9, No. 2, Dec. 19, 2015, p. 169-186.
Marjie L. Hard et al., “Pharmacokinetic Evaluation of a 1-Day Treatment Initiation Option . . . ” Journal of Clinical Psychopharmacology, vol. 38, No. 5, Oct. 1, 2018, pp. 435-441.
Wang X et al., “The two-injection start of aripiprazole once-monthly provide rapid . . . ,” European Neuropsychopharmacology, Elsevier Science Publishers BV, vol. 40, Nov. 1, 2020.
International Search Report dated Jul. 8, 2021, PCT/JP2021/014194.
International Report on Patentability dated Sep. 29, 2022, PCT/JP2021/014194.
L. Rahnfeld et al., Injectable Lipid-Based Depot Formulations: Where Do We Stand?, Pharmaceutics 2020, 12, 0567, 28 pages.
Abilify Maintena SmPC, 2018, 23 pages.
R. Jain et al., Size matters: the importance of particle size in a newly developed injectable formulation for the treatment of schizophrenia, CNS Spectrums, 2019, 8 pages.
Abilify Maintena, EMA/737723/2013, EMA Assessment Report, 12 pages.
S. Hiraoka et al., Preparation and Characterization of High-Content Aripiprazole-Loaded Core—Shell Structure Microsphere for Long-Release Injectable Formulation, Chem. Pharm. Bull., vol. 62, No. 7, 2014, pp. 654-660.
Extended European Search Report, Application No. 24205231.4, dated Dec. 10, 2024.
Fagiolini et al., Adv Ther (2025) 42:1935-1949, Abstract.
Orsolini et al., Asian Journal of Psychiatry 94 (2024) 103992, Abstract.
European Psychiatry, (Jun. 2022) vol. 65, Supp. Supplement 1, pp. S796, EPV 1432.
European Psychiatry, (Jun. 2022) vol. 65, Supp. Supplement 1, pp. S788-S789, EPV 1406.
European Psychiatry, (Mar. 2023) vol. 66, Supp. Supplement 1, pp. S1044, EPV0916.
Trovini et al., Int. J. Mol. Sci. 2025, 26, 1394.
Bioque et al., Journal of Psychiatric Practice 30(2) p. 82-94, Mar. 2024.
Salvi et al., Neuropsychopharmacology reports, 2022;001-4.
Wang et al., Current Medical Research and Opinion 2021 Vol. 37 No. 11 pp. 1961-1972,1969.
Rapinesi, C. et al., Clinical Drug Investigation, May 31, 2019, vol. 39, pp. 713-735.
Search Report and Written Opinion dated Aug. 22, 2025, Singapore Application No. 11202253274F.
Otsuka Pharmaceutical Co., Ltd. Communication of notices of opposition (R. 79(1) EPC), Application No./Patent No. 21720012.0-1109 / 4125903; Reference 246 436 a/dst; Jul. 21, 2205.
Otsuka Pharmaceutical Co., Ltd. Communication of a notice of opposition, Application No./Patent No. 21720012.0-1109 / 4125903; Reference 246 436 a/dst; Jul. 11, 2205.
Otsuka Pharmaceutical Co., Ltd. Communication of a notice of opposition, Application No./Patent No. 21720012.0-1109 / 4125903; Reference 246 436 a/dst; July 7, 2205.
Otsuka Pharmaceutical Co., Ltd. Communication of a notice of opposition, Application No./Patent No. 21720012.0-1109 / 4125903; Reference 246 436 a/dst; Jul. 15, 2025.
Otsuka Pharmaceutical Co., Ltd. Communication of a notice of opposition, Application No./Patent No. 21720012.0-1109 / 4125903; Reference 246 436 a/dst; Jul. 9, 2025.
Hard et al., Pharmacokinetics and safety of deltoid or gluteal injection of aripiprazole lauroxil NanoCrystal® Dispersion used for initiation of the long-acting antipsychotic aripiprazole lauroxil, Therapeutic Advances in Psychopharmacology 2019, vol. 9, p. 1-9, (Year: 2019).
Raoufinia.et al., Aripiprazole Once-Monthly 400 mg: Comparison of Pharmacokinetics, Tolerability, and Safety of Deltoid Versus Gluteal Administration, International Journal of Neuropsychopharmacology (2017) 20(4): 295-304, doi:10.1093/ijnp/pyw116 (Year: 2017).
Ansel et al., Pharmaceutical Dosage Forms and Drug Delivery Systems, 7th ed., A Wolters Kluwer Company, 1999, p. 48-53, Year 1999.
J. M. Meyer, “Aripiprazole lauroxil nanocrystal suspension”, Current Psychiatry, 2018, vol. 17, No. 1, pp. 34-40, published: Nov. 2018.
M. L. Hard et al., “Population Pharmacokinetic Analysis and Model-Based Simulations of Aripiprazole for a 1-Day Initiation Regimen for the Long-Acting Antipsychotic Aripiprazole Lauroxil”, Eur. J. Drug Metab. Pharmacokinet., 2018, vol. 43, pp. 461-469, published: Jun. 11, 2018.
Australian Register of Therapeutic Goods, Product Information: Ability Maintena®, pp. 1-29, published: Nov. 25, 2014.
U.S. Department of Health and Human Services, FDA, “Population Pharmacokinetics Guidance for Industry”, Jul. 2019, pp. 1-23, published: Jul. 2019.
U. Hopkins et al., “Large-volume IM injections: A review of best practices”, Oncology Nurse Advisor, Jan./Feb. 2013, pp. 32-37, published: Feb. 2013.
Abilify Maintena ®: Type II variation assessment report, European Medicines Agency, Sep. 17, 2020.
Abilify Maintena ®: Printout from the Union Register of medicinal products for human use, Jun. 4, 2025.
Decision C(2020) 7576 of the European Commission, Oct. 27, 2020.
Official Journal of the European Union 63 (2020), C 409.
Abilify Maintena ®: EP AR—Summary for the public, European Medicines Agency, Nov. 2020.
L.A. Raedler et al., „Aripiprazole Lauroxil (Aristada): Long-Acting Atypical Antipsychotic Injection Approved for the Treatment of Patients with Schizophrenia, American Health & Drug Benefits, vol. 9, Mar. 2016, pp. 40-43, published: Mar. 2016.
Meyer, Jonathan, “A new Method for initiating Treatment with the Longacting Antipsychotic Aripiprazole Lauroxil” CNS Sprectrums, vol. 24, No. 1, 2019 articular relevance: 188-189.
Public Assessment Report of the European Medicines Agency for Ability Maintena EMEA/H/C/002755/0000, Sep. 19, 2013.
Highlights of Prescribing Information for Abilify Maintena. Abilify Maintena® (aripiprazole) for extended-release injectable suspension, for intramuscular use; Food and Drug Administration, version

(56) References Cited

OTHER PUBLICATIONS

"Jan. 2020", published on Feb. 5, 2020, see "Approval Date(s) and History, Letters, Labels, Reviews for NOA 202971" on https://www.accessdata.fda.gov.
Highlights of Prescribing Information; Aristada® (aripiprazole lauroxil) extended-release injectable suspension, for intramuscular use; Food and Drug Administration; Nov. 2018.
Pharmacokinetics and safety of deltoid or gluteal injection of aripiprazole lauroxil NanoCrystal® Dispersion used for initiation of the long-acting antipsychotic aripiprazole lauroxil; Marjie L. Hard et al., Ther Adv Psychopharmacol; 2019, vol. 9: 1-9.
Plasma concentrations and dosing of 2 long-acting injectable formulations of aripiprazole; Salzman et al.; Neuropsychiatric Disease and Treatment; Apr. 20, 2017 Volume 2017:13 pp. 1125-1129.
Excerpt from online dictionary Wikipedia titled "Injection (medicine)" dated Mar. 24, 2020.
Excerpt from Abstract Book—Posters for the ASCP Annual Meeting on Jun. 22-25, 2015: Peters-Strickland, T.; et al. W86 Deltoid Injection of Aripiprazole Once-Monthly in the Treatment of Schizophrenia.
Press Release: FDA Approves Deltoid Injection Site for Ability Maintena® (aripirprazole) for extended-release injectable suspension in the Treatment of Schizophrenia. Jul. 30, 2015.
Brissos, S.; et al. The role of long-acting injectable antipsychotics in schizophrenia: a critical appraisal. Ther. Adv. Psychopharmacol. 2014, 4, 198-219.
Hughes, M. Long-Acting Injectable (LAI) Dosing Chart; updated on Jan. 1, 2019.
Excerpt from online dictionary Wikipedia titled "Low dead space syringe" dated Sep. 30, 2019.
Bartova, L.; et al. Ultra-High-Dose Long-Acting Injectable Aripiprazole in Chronic Refractory Schizophrenia: A Case Report. J. Clin. Toxicol. 2015, 5, 270.
FDA Highlights of prescribing information of Aristada Initiotm revised Jun. 2018.
Press release of Lundbeck: Health Canada Approves Otsuka and Lundbeck's Abilify Maintena® (aripiprazole for prolonged release injectable suspension) Alternative Initiation Regimen of Mar. 3, 2021.
Abilify Maintena ®, US-Label Jul. 2017.
J.M. Meyer, CNS Spectrums 22 (2017), 17-27.
S.J. Shah et al., World Journal of Phannaceutical Research 4(8) (2015), 724-47.
S. Ahmad et al., International Journal of Scientific Research 12(4) (2015), 367-372.
Q. Cai et al., European Journal of Phannaceutical Sciences 125 (2018), 193-204.
X. Guo et al., International Journal of Pharmaceutics 612 (2022), 121300.
V.T.T. Nguyen et al., The AAPS Journal 25 (2022), 4.
English machine translation of CN 110 327 296 A.
Annexes I to III of Decision C(2019) 3387 of the European Commission, Apr. 29, 2019.
M.J. Ehret et al., Clinical Schizophrenia & Related Psychoses 2018, 92-96.
ARISTADA ®, US-Label Jun. 2017.
Hebbrecht et al., Expert Opinion on Drug Metabolism & Toxicology, vol. 14, Nos. 7-12, 2018, 999-1005, "Pharmacokinetic evaluation of the aripiprazole (once-monthly) injection for the treatment of bipolar disorder".
Excerpt Rote Liste 2019, Entry No. 71 091.
Federal Register / vol. 84, No. 134 / Friday, Jul. 12, 2019.
Biol. Pharm. Bull. 30(11) 2154-2158 (2007), "Nonlinear Mixed Effects Model Analysis of the Pharmacokinetics of Aripiprazole in Healthy Japanese Males".
Br J Clin Pharmacol / 66:6 / 802-810 (2008), "Population pharmacokinetic modelling of aripiprazole and its active metabolite, dehydroaripiprazole, in psychiatric patients".
Product Monograph, Ablify Maintena, Mar. 2, 2021.
FDA New Drug Application 207533, Summary Review (available under https://www.accessdata. fda.gov/drugsatfda_docs/nda/2015/207533Orig1s000SumR.pdf), Oct. 2, 2015.
New Drug Application 207533, Clinical Review, Oct. 2, 2015.
Press release "FDA Approves Aristada Tm (aripiprazole lauroxil), a Long-acting Injectable Drug to Treat Schizophrenia (US)", Oct. 14, 2015.
SmPC of paliperidone palmitate, Dec. 16, 2015.

* cited by examiner

[Fig. 1]

1st Deltoid IM Administration

5th Deltoid IM Administration

| Table 2.7.2.5.1-1 Purpose and Description of Simulations | | |
|---|---|---|
| Simulation Purpose | Number | Simulation Scenario |
| To compare the existing initiation regimens (g1 & g2 or d1 & d2) with other initiation regimens where 20 mg Oral + 2x300, 300+400, or 2x400 mg IM Depot were administered | g1 | 10 mg Oral (14 days) + 400 mg Gluteal (Day 1) |
| | g2 | 20 mg Oral (14 days) + 400 mg Gluteal (Day 1) |
| | g5 | 20 mg Oral (Day 1) + 2x400 mg Gluteal (Day 1) |
| | d1 | 10 mg Oral (14 days) + 400 mg Deltoid (Day 1) |
| | d2 | 20 mg Oral (14 days) + 400 mg Deltoid (Day 1) |
| | d5 | 20 mg Oral (Day 1) + 2x400 mg Deltoid (Day 1) |
| | g1 | 10 mg Oral (14 days) + 400 mg Gluteal (Day 1) |
| | g2 | 20 mg Oral (14 days) + 400 mg Gluteal (Day 1) |
| | g11sim4x | 20 mg Oral (Day 1) + 400 mg IM Depot Gluteal (Day 1) + 400 mg IM Depot Deltoid (Day 1) |
| | d1 | 10 mg Oral (14 days) + 400 mg Deltoid (Day 1) |
| | d2 | 20 mg Oral (14 days) + 400 mg Deltoid (Day 1) |
| | g1 | 10 mg Oral (14 days) + 400 mg Gluteal (Day 1) |
| | g2 | 20 mg Oral (14 days) + 400 mg Gluteal (Day 1) |
| | g3 | 20 mg Oral (Day 1) + 2x300 mg Gluteal (Day 1) |
| | g4 | 20 mg Oral (Day 1) + 400 + 300 mg Gluteal (Day 1) |
| | g5 | 20 mg Oral (Day 1) + 2x400 mg Gluteal (Day 1) |
| | d1 | 10 mg Oral (14 days) + 400 mg Deltoid (Day 1) |
| | d2 | 20 mg Oral (14 days) + 400 mg Deltoid (Day 1) |
| | d3 | 20 mg Oral (Day 1) + 2x300 mg Deltoid I (Day 1) |
| | d4 | 20 mg Oral (Day 1) + 400 + 300 mg Deltoid (Day 1) |
| | d5 | 20 mg Oral (Day 1) + 2x400 mg Deltoid (Day 1) |
| To compare the existing initiation regimens (g1 & g2 or d1 & d2) with other initiation regimens where 10, 20, or 30 mg Oral + 2x400 mg IM Depot were administered | g1 | 10 mg Oral (14 days) + 400 mg Gluteal (Day 1) |
| | g2 | 20 mg Oral (14 days) + 400 mg Gluteal (Day 1) |
| | g6 | 10 mg Oral (Day 1) + 2x400 mg Gluteal (Day 1) |
| | g5 | 20 mg Oral (Day 1) + 2x400 mg Gluteal (Day 1) |
| | g7 | 30 mg Oral (Day 1) + 2x400 mg Gluteal (Day 1) |
| | d1 | 10 mg Oral (14 days) + 400 mg Deltoid (Day 1) |
| | d2 | 20 mg Oral (14 days) + 400 mg Deltoid (Day 1) |
| | d6 | 10 mg Oral (Day 1) + 2x400 mg Deltoid (Day 1) |
| | d5 | 20 mg Oral (Day 1) + 2x400 mg Deltoid (Day 1) |
| | d7 | 30 mg Oral (Day 1) + 2x400 mg Deltoid (Day 1) |
| To show separate contribution from oral and IM Depot formulation (one or two injections) to the initiation regimens | g8 | 20 mg Oral (Day 1) |
| | g10 | 400 mg Gluteal (Day 1) |
| | d10 | 400 mg Deltoid (Day 1) |
| | g8 | 20 mg Oral (Day 1) |
| | g9 | 2x400 mg Gluteal (Day 1) |
| | g8 | 20 mg Oral (Day 1) |
| | d9 | 2x400 mg Deltoid (Day 1) |

FIG. 3A

| Table 2.7.2.5.1-1 Purpose and Description of Simulations | | |
|---|---|---|
| Simulation Purpose | Number | Simulation Scenario |
| To show Cmax distribution and PK profiles following alternate initiation regimens with 2x300 mg or 2x400 mg IM Depot doses compared between the poor and extensive CYP2D6 metabolizers | g5 | 20 mg Oral (Day 1) + 2x400 mg Gluteal (Day 1) [EM] |
| | g5p | 20 mg Oral (Day 1) + 2x400 mg Gluteal (Day 1) [PM] |
| | g11 | 20 mg Oral (Day 1) + 2x300 mg Gluteal (Day 1) [PM] |
| | d5 | 20 mg Oral (Day 1) + 2x400 mg Deltoid (Day 1) [EM] |
| | d5p | 20 mg Oral (Day 1) + 2x400 mg Deltoid (Day 1) [PM] |
| | d11 | 20 mg Oral (Day 1) + 2x300 mg Deltoid (Day 1) [PM] |
| To compare PK profile between the existing initiation regimen and the initiation regimen with 20mg oral + 2x400 IM Depot dose when administered in subjects who were already stabilized on oral aripiprazole (10 -30 mg) before initiating treatment with the IM Depot formulation | g12 | 10 mg Oral (ss) + 10 mg Oral (14 days) + 400 mg Gluteal (Day 1) |
| | g14 | 10 mg Oral (ss) + 20 mg Oral (Day 1) + 2x400 mg Gluteal (Day 1) |
| | g13 | 20 mg Oral (ss) + 20 mg Oral (14 days) + 400 mg Gluteal (Day 1) |
| | g15 | 20mg Oral (ss) + 20 mg Oral (Day 1) + 2x400 mg Gluteal (Day 1) |
| | g5x | 30 mg Oral (ss) + 20 mg Oral (14 days) + 400 mg Gluteal (Day 1) |
| | g13x | 30mg Oral (ss) + 20 mg Oral (Day 1) + 2x400 mg Gluteal (Day 1) |
| | d12 | 10 mg Oral (ss) + 10 mg Oral (14 days) + 400 mg Deltoid (Day 1) |
| | d14 | 10 mg Oral (ss) + 20 mg Oral (Day 1) + 2x400 mg Deltoid (Day 1) |
| | d13 | 20 mg Oral (ss) + 20 mg Oral (14 days) + 400 mg Deltoid (Day 1) |
| | d15 | 20mg Oral (ss) + 20 mg Oral (Day 1) + 2x400 mg Deltoid (Day 1) |
| | d5x | 30 mg Oral (ss) + 20 mg Oral (14 days) + 400 mg Deltoid (Day 1) |
| | d13x | 30mg Oral (ss) + 20 mg Oral (Day 1) + 2x400 mg Deltoid (Day 1) |
| To compare PK profile between the existing initiation regimen and the initiation regimen with 20 mg oral + 2x300 or 2x400 mg IM Depot dose in subjects who were already stabilized on oral aripiprazole (30 mg [EM] or 15 mg [PM]) before initiating treatment with the IM Depot formulation | g5x | 30 mg Oral (ss) + 20 mg Oral (1 day) + 400 mg Gluteal (Day 1) [EM] |
| | g5px2 | 15 mg Oral (ss) + 20 mg Oral (Day 1) + 2x400 mg Gluteal (Day 1) [PM] |
| | g11x2 | 15 mg Oral (ss) + 20 mg Oral (Day 1) + 2x300 mg Gluteal (Day 1) [PM] |
| | d5x | 30 mg Oral (ss) + 20 mg Oral (1 day) + 400 mg Deltoid (Day 1) [EM] |
| | d5px2 | 15 mg Oral (ss) + 20 mg Oral (Day 1) + 2x400 mg Deltoid (Day 1) [PM] |
| | d11x2 | 15 mg Oral (ss) + 20 mg Oral (Day 1) + 2x300 mg Deltoid (Day 1) [PM] |

FIG. 3B

| Table 2.7.2.5.1-1 Purpose and Description of Simulations | | |
|---|---|---|
| Simulation Purpose | Number | Simulation Scenario |
| To compare PK profile between the existing initiation regimen and the initiation regimen with 20 mg oral + 2x300 or 2x400 mg IM Depot dose in subjects who were already stabilized on oral aripiprazole (20 mg [EM] or 10 mg [PM]) before initiating treatment with the IM Depot formulation | g15 | 20 mg Oral (ss) + 20 mg Oral (1 day) + 400 mg Gluteal (Day 1) [EM] |
| | g5px3 | 10 mg Oral (ss) + 20 mg Oral (Day 1) + 2x400 mg Gluteal (Day 1) [PM] |
| | g11x3 | 10 mg Oral (ss) + 20 mg Oral (Day 1) + 2x300 mg Gluteal (Day 1) [PM] |
| | d15 | 20 mg Oral (ss) + 20 mg Oral (1 day) + 400 mg Deltoid (Day 1) [EM] |
| | d5px3 | 10 mg Oral (ss) + 20 mg Oral (Day 1) + 2x400 mg Deltoid (Day 1) [PM] |
| | d11x3 | 10 mg Oral (ss) + 20 mg Oral (Day 1) + 2x300 mg Deltoid (Day 1) [PM] |
| To compare PK following initiation and re-initiation with 20 mg oral + 2x400 mg IM Depot dose (an alternative initiation regimen) vs the existing initiation regimen when the second or third IM Depot dose was missed, and it has been 5 weeks since the last IM Depot dose | g19 | Missed 2nd Dose- Re-initiation with 20 mg oral (Day 1) + 2x400 mg IM (Day 1) [Gluteal] |
| | g20 | Missed 2nd Dose- Re-initiation with 20 mg oral (14 days) + 400 mg IM (Day 1) [Gluteal] |
| | g21 | Missed 3rd Dose- Re-initiation with 20 mg oral (Day 1) + 2x400 mg IM (Day 1) [Gluteal] |
| | g22 | Missed 3rd Dose- Re-initiation with 20 mg oral (14 days) + 400 mg IM (Day 1) [Gluteal] |
| | d19 | Missed 2nd Dose- Re-initiation with 20 mg oral (Day 1) + 2x400 mg IM (Day 1) [Deltoid] |
| | d20 | Missed 2nd Dose- Re-initiation with 20 mg oral (14 days) + 400 mg IM (Day 1) [Deltoid] |
| | d21 | Missed 3rd Dose- Re-initiation with 20 mg oral (Day 1) + 2x400 mg IM (Day 1) [Deltoid] |
| | d22 | Missed 3rd Dose- Re-initiation with 20 mg oral (14 days) + 400 mg IM (Day 1) [Deltoid] |
| To compare PK following initiation and reinitiation with 20 mg oral + 2 x 400 mg IM depot dose (an alternative initiation regimen) vs the existing initiation regimen when the fourth or a steady state IM depot dose was missed, and it has been 6 weeks since the last IM depot dose | g23 | Missed 4th Dose- Re-initiation with 20 mg oral (Day 1) + 2x400 mg IM (Day 1) [Gluteal] |
| | g24 | Missed 4th Dose- Re-initiation with 20 mg oral (14 days) + 400 mg IM (Day 1) [Gluteal] |
| | g25 | Missed ss Dose- Re-initiation with 20 mg oral (Day 1) + 2x400 mg IM (Day 1) [Gluteal] |
| | g26 | Missed ss Dose- Re-initiation with 20 mg oral (14 days) + 400 mg IM (Day 1) [Gluteal] |
| To compare PK following initiation and re-initiation with 20 mg oral + 2x400 mg IM Depot dose (an alternative initiation regimen) vs the existing initiation regimen when the fourth or a steady state IM Depot dose was missed, and it has been 6 weeks since the last IM Depot dose | d23 | Missed 4th Dose- Re-initiation with 20 mg oral (Day 1) + 2x400 mg IM (Day 1) [Deltoid] |
| | d24 | Missed 4th Dose- Re-initiation with 20 mg oral (14 days) + 400 mg IM (Day 1) [Deltoid] |
| | d25 | Missed ss Dose- Re-initiation with 20 mg oral (Day 1) + 2x400 mg IM (Day 1) [Deltoid] |
| | d26 | Missed ss Dose- Re-initiation with 20 mg oral (14 days) + 400 mg IM (Day 1) [Deltoid] |

FIG. 3C

Missed 2nd Gluteal IM Administration

Missed 4th Gluteal IM Administration

Missed 4th Deltoid IM Administration

METHODS FOR DOSE INITIATION OF ARIPIPRAZOLE TREATMENTS

This application is a continuation application of U.S. application Ser. No. 17/907,583, filed Sep. 28, 2022, which is a national stage filing under 35 U.S.C. § 371 of International Application No. PCT/JP2021/014194, filed on Apr. 1, 2021, and claims priority to U.S. Provisional Application No. 63/003,544, filed Apr. 1, 2020; the disclosure of each of these applications are incorporated herein by reference in their entirety.

TECHNICAL FIELD

Background Art

Aripiprazole, a partial agonist at the dopamine (D2) and serotonin 5-HT1A receptors, and an antagonist at serotonin 5-HT2A receptors, is an atypical antipsychotic that has demonstrated efficacy in clinical trials for the treatment of schizophrenia and bipolar I disorder in adults. Abilify Maintena(R), the intramuscular (IM) depot formulation of aripiprazole, is a prolonged-release suspension for injection. It is approved in many countries for the maintenance treatment of schizophrenia in adult patients stabilized with oral aripiprazole.

SUMMARY OF INVENTION

Technical Problem

Aripiprazole once monthly is a long acting IM injectable formulation of aripiprazole indicated for maintenance treatment of schizophrenia and bipolar I disorder in adult patients stabilized on oral aripiprazole. In the currently approved label for Abilify Maintena(R), a first dose is administered with concomitant oral aripiprazole (10 mg to 20 mg) for fourteen consecutive days to adult patients stabilized with oral aripiprazole. In patient populations considered to be at potential risk for adherence-related relapse or suboptimal treatment outcomes (e.g., long acting injectable (LAI) patient population), achieving therapeutic plasma concentrations may offer a treatment advantage.

Solution to Problem

To provide an additional option for this initiation stage, a two-injection start initiation regimen comprising two, separate administrations of aripiprazole once-monthly at separate gluteal and/or deltoid injection sites with a single oral dose of aripiprazole on the first day of treatment is provided based on population pharmacokinetic (popPK) modeling and simulation. For example, the present disclosure is directed to an alternative initiation regimen of two, separate administrations of an aripiprazole intramuscular (IM) depot formulation, such as Abilify Maintena(R), together with a shorter oral overlap. Simulations of the alternative initiation regimen of two injections of an aripiprazole intramuscular (IM) depot formulation at separate gluteal and/or deltoid injection sites together with a single oral aripiprazole on the first day of treatment is shown to be sufficient and the alternative initiation regimen may be an additional option for initiation of Abilify Maintena(R).

In some aspects, the present disclosure is directed to a method of dose initiation for an aripiprazole treatment to a patient in need thereof comprising: administering two, separate injections of an aripiprazole intramuscular (IM) depot formulation, wherein each injection comprises from about 10 mg to about 500 mg of aripiprazole to the patient at separate gluteal and/or deltoid injection sites, and a single dose of oral aripiprazole, wherein the step of administering occurs on a first day of the treatment.

In additional aspects, each of the two, separate injections comprises about 400 mg of aripiprazole. Additionally, the methods of the present disclosure further comprise after the first day of treatment, administering a single monthly, maintenance injection of the aripiprazole IM depot formulation. For example, in other aspects, the single monthly, maintenance injection is chosen from about 300 mg and about 400 mg of aripiprazole in the aripiprazole IM depot formulation. In further aspects, when the patient is a CYP2D6 poor metabolizer or is taking concomitant CYP3A4 inhibitors or CYP2D6 inhibitors for greater than 14 days, the single monthly, maintenance injection is chosen from 160 mg and 200 mg of aripiprazole in the aripiprazole IM depot formulation.

In further aspects, the two, separate injections of the aripiprazole IM depot formulation are administered at separate gluteal injection sites of the patient. Additionally, the two, separate injections of the aripiprazole IM depot formulation are administered at a gluteal injection site and a deltoid injection site of the patient. Further for example, the two, separate injections of the aripiprazole IM depot formulation are administered at separate deltoid injection sites of the patient.

In aspects of the present disclosure, the patient has schizophrenia. In other aspects, the patient has bipolar 1 disorder.

In some further aspects, the single dose of oral aripiprazole ranges from about 2 mg to about 30 mg of aripiprazole. For example, the single dose of oral aripiprazole ranges from about 10 mg to about 30 mg. Additionally, for example, the single dose of oral aripiprazole is 20 mg. And, in some further aspects, the single dose of oral aripiprazole is 10 mg.

In some further aspects, when the patient is a CY2D6 poor metabolizer, each of the two, separate injections comprises about 300 mg of aripiprazole and the single dose of oral aripiprazole is about 20 mg.

In some further aspects, the present disclosure is directed to an aripiprazole intramuscular (IM) depot formulation comprising from about 10 mg to about 500 mg of aripiprazole, for use in administering two, separate injections of the aripiprazole intramuscular (IM) depot formulation to a patient in need thereof at an injection site chosen from a gluteal site, a deltoid site, and combinations thereof, in combination with a single dose of oral aripiprazole, wherein the step of administering occurs on a first day of the treatment.

In some further aspects, the present disclosure is directed to aripiprazole or a salt thereof for use in the treatment of schizophrenia or bipolar I disorder, wherein aripiprazole or a salt thereof is to be administered to a patient in need thereof by any one of the methods of dose initiation for an aripiprazole treatment of the present disclosure. Additionally, the present disclosure also provides use of aripiprazole or a salt thereof in the manufacture of a medicament, wherein aripiprazole or a salt thereof is to be administered to a patient in need thereof by any one of the methods of dose initiation for an aripiprazole treatment of the present disclosure.

BRIEF DESCRIPTION OF DRAWINGS

FIGS. 3A-3C is a table of the purpose and description of the simulations.

DESCRIPTION OF EMBODIMENTS

Figure 1:
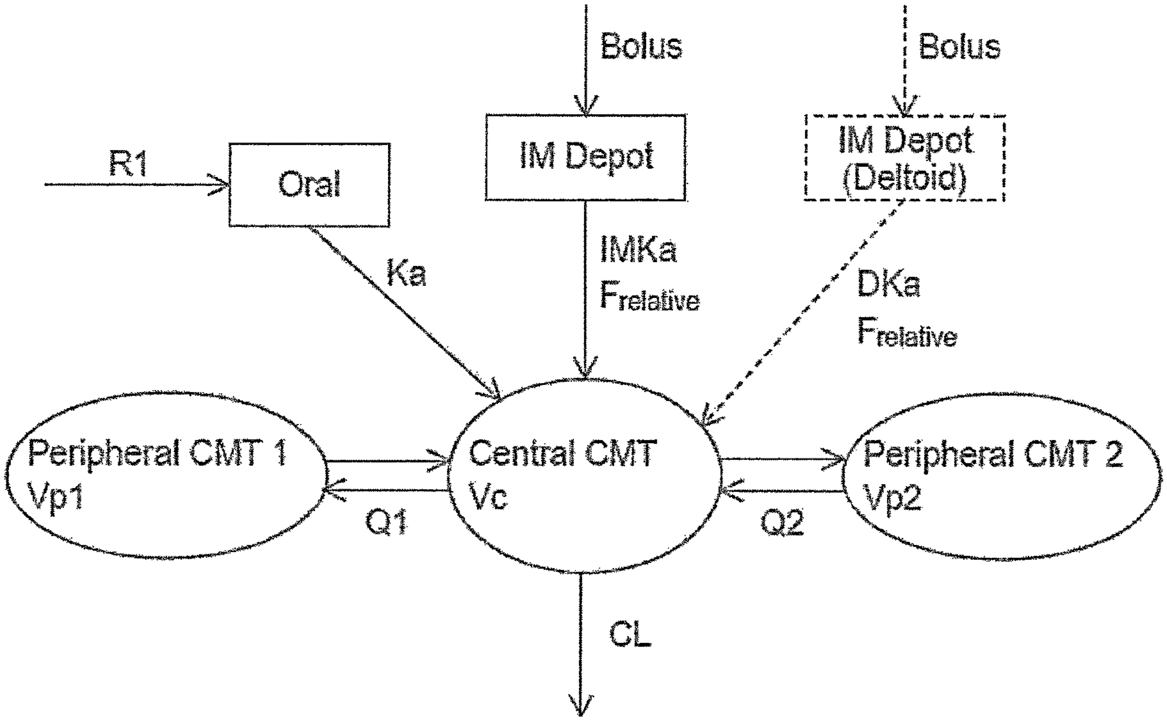
FIG. 1 is a diagram of the structural model describing aripiprazole PK following oral administration and IM injection in gluteal and deltoid muscles.
Figure 2A:
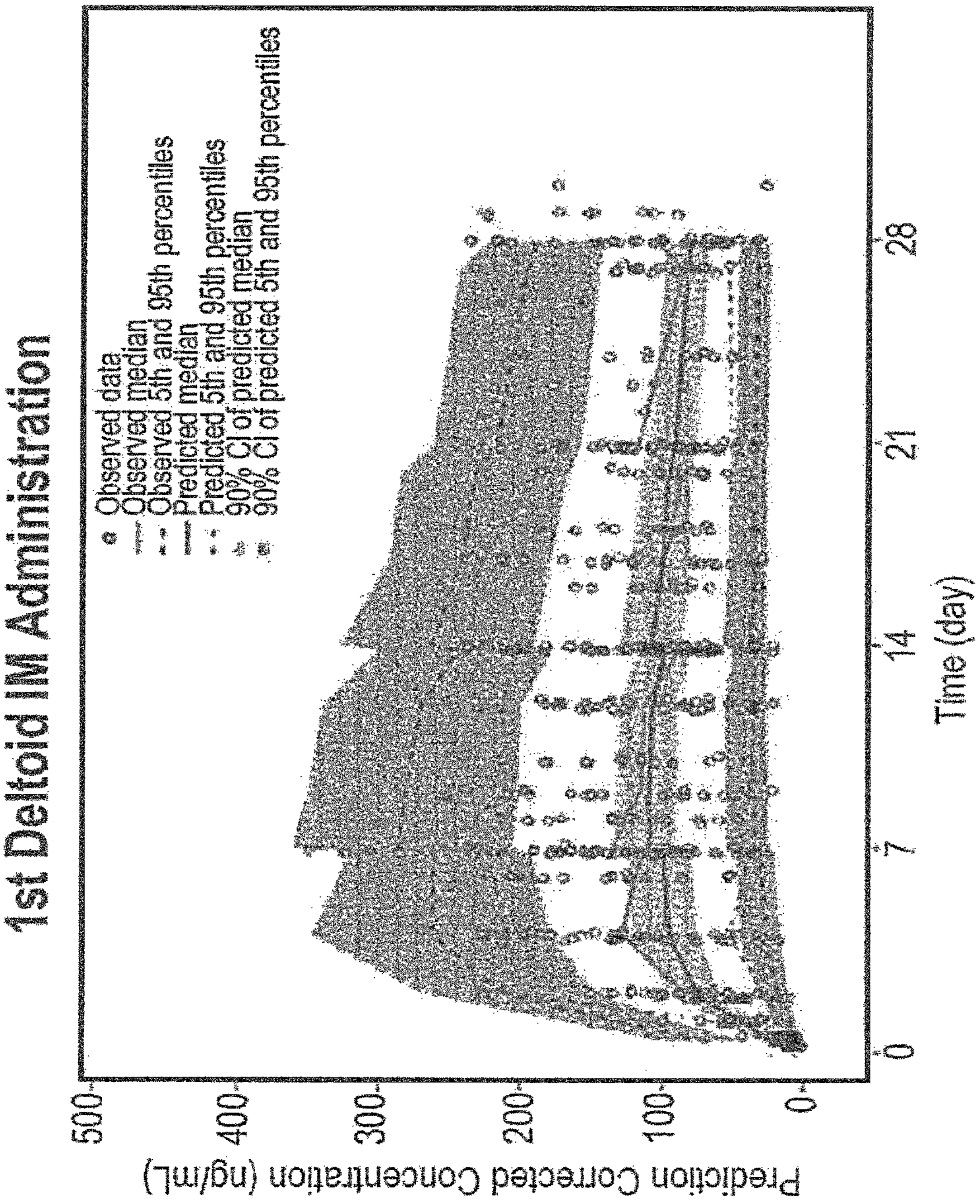
FIGS. 2A-2D are diagrams of prediction corrected visual predictive check of the final combined population pharmacokinetic (popPK) model.
Figure 2B:
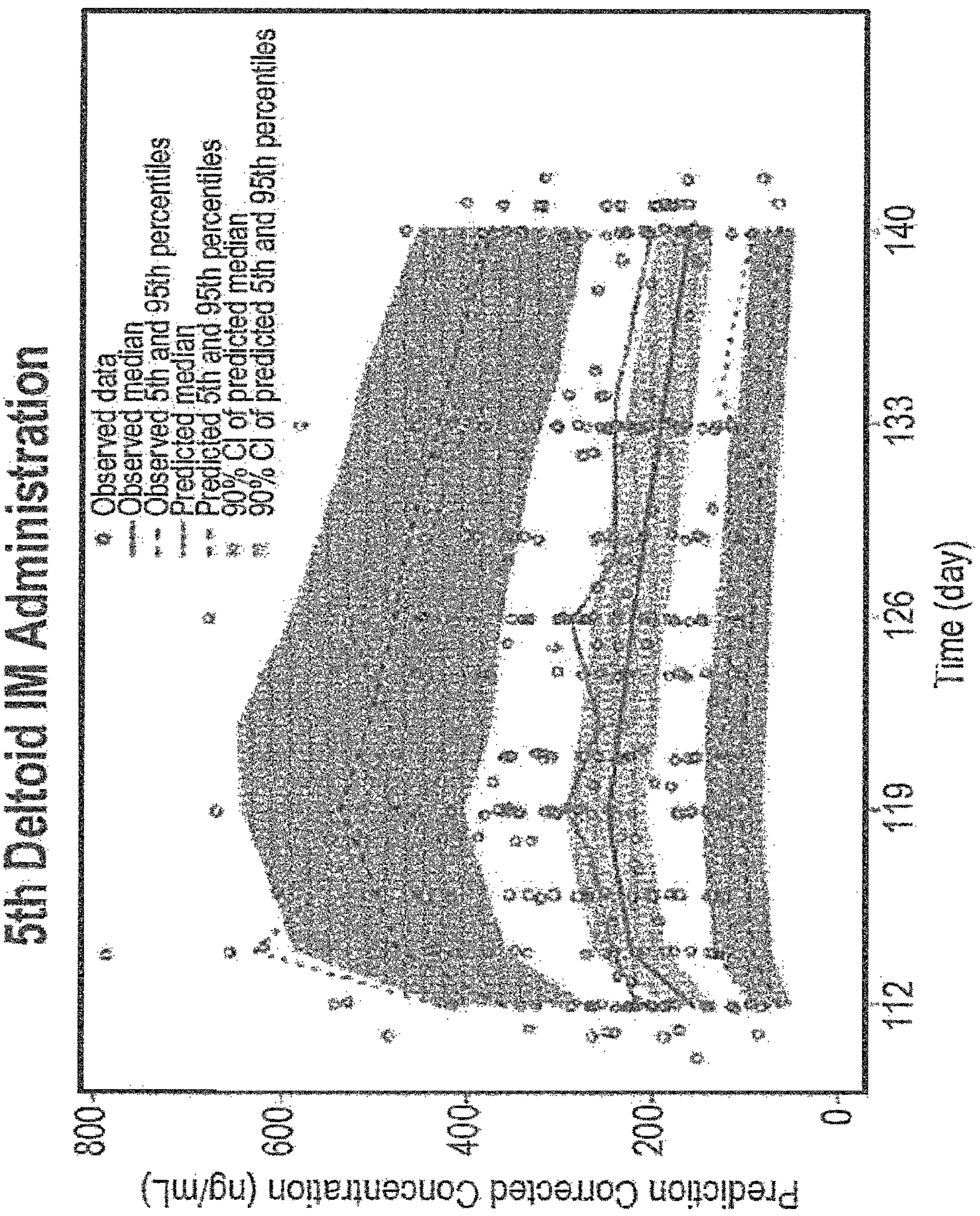
Figure 2C:
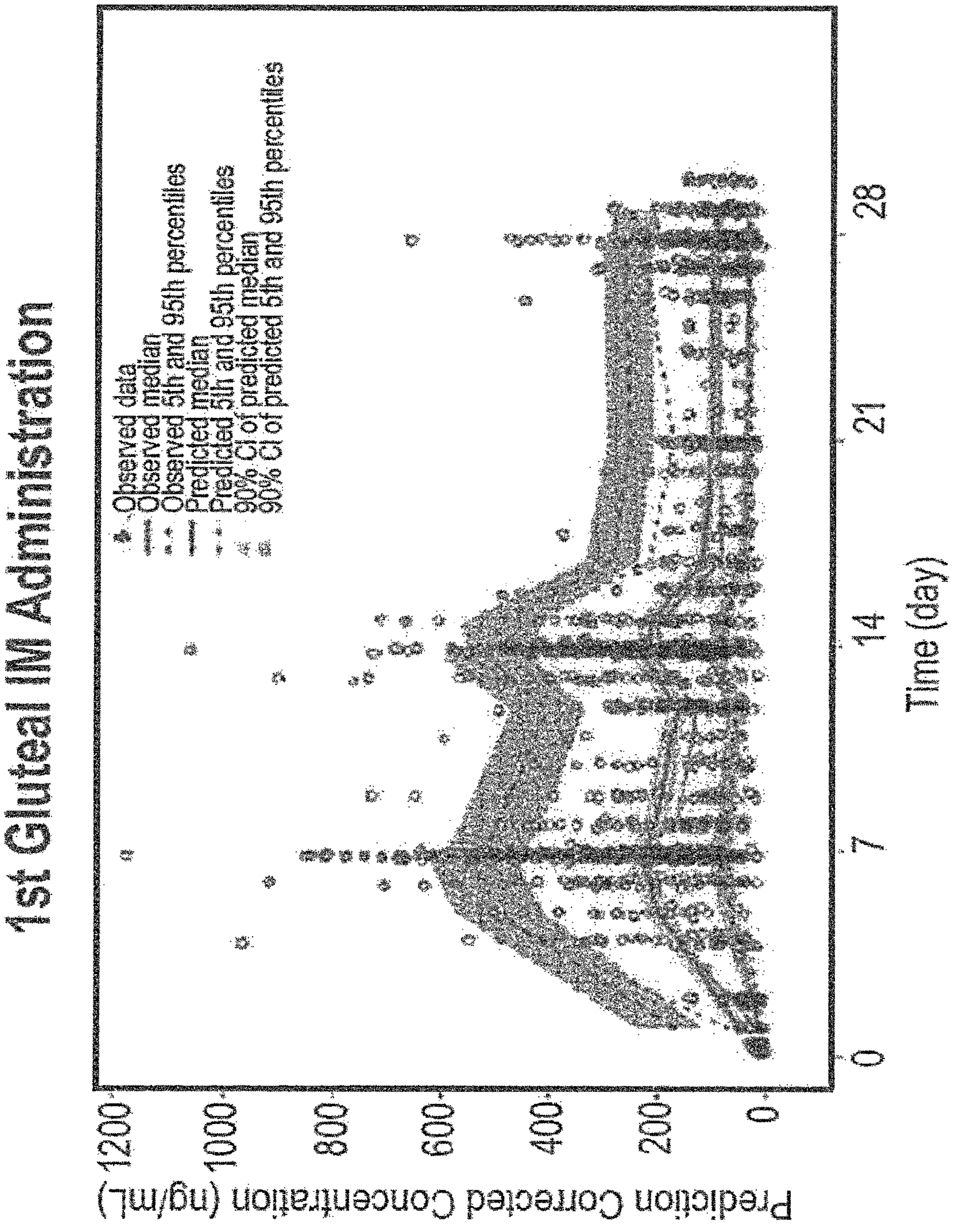
Figure 2D:
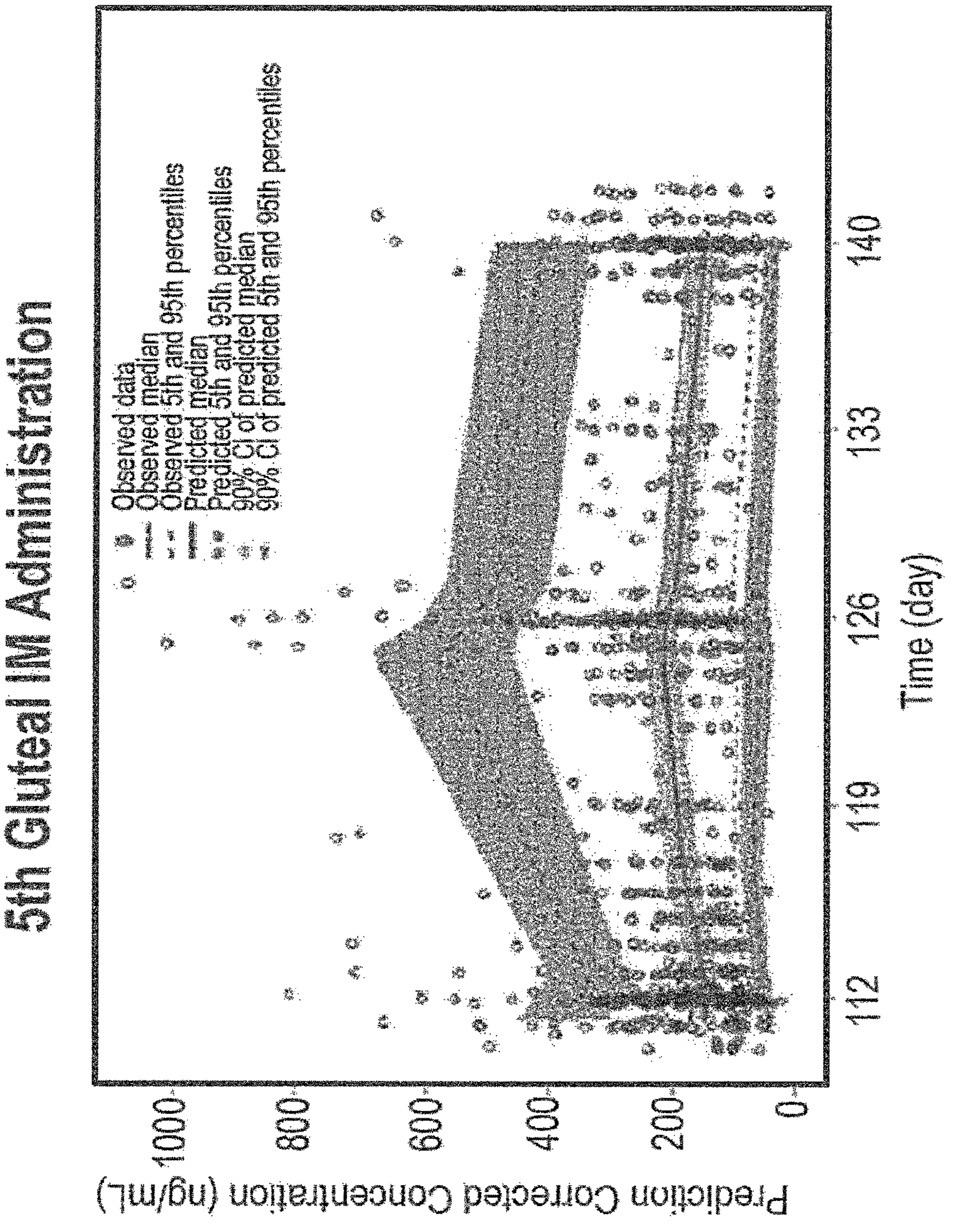
Figure 4A:
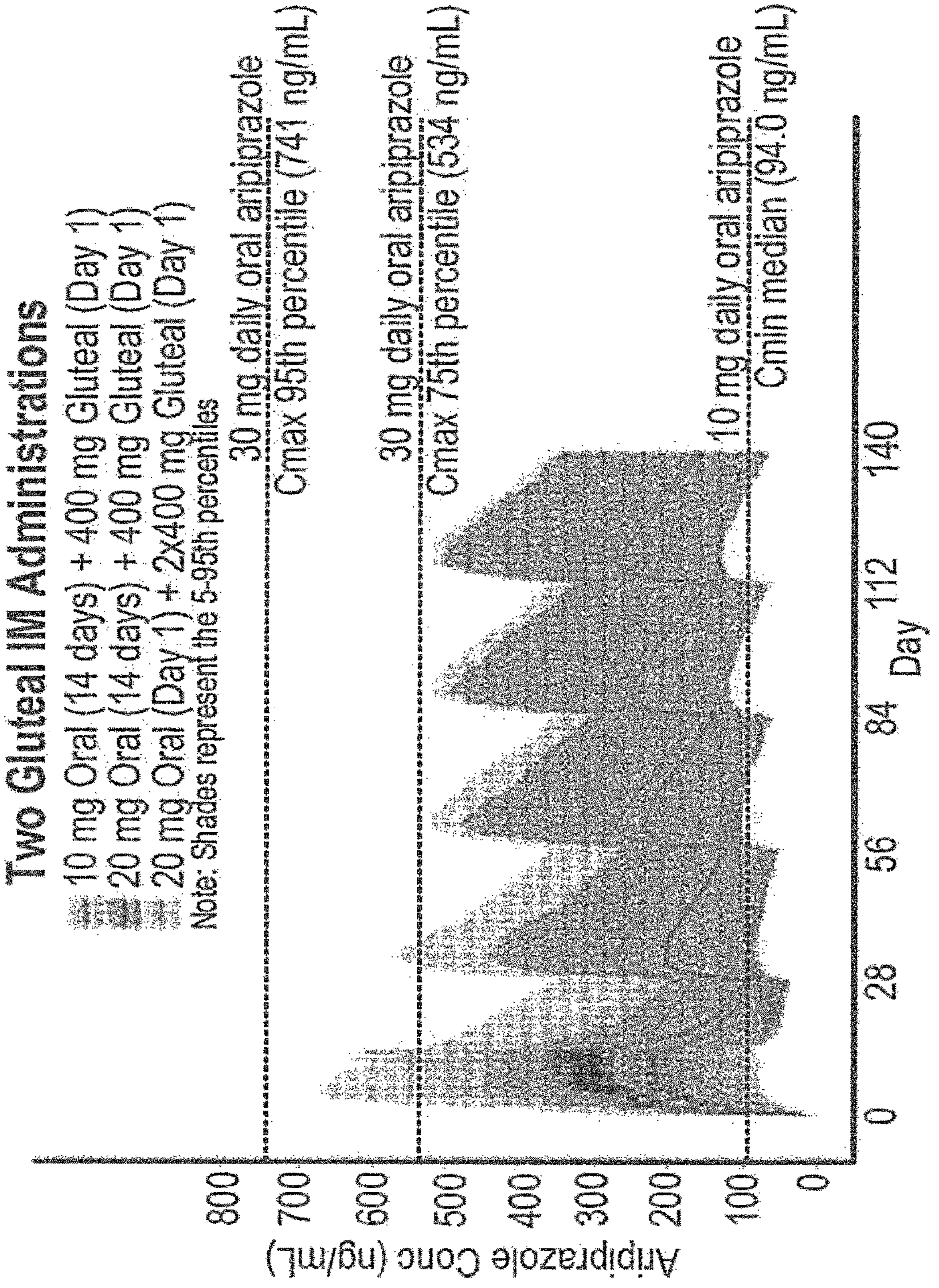
FIGS. 4A-4D are diagrams of simulated median ($5^{th}$-$95^{th}$ percentile) aripiprazole concentration time profile following the current or alternative initiation regimen, followed by 400 mg intramuscular depot dose every 28 days. The shades represent the $5^{th}$-$95^{th}$ percentiles.
Figure 4B:
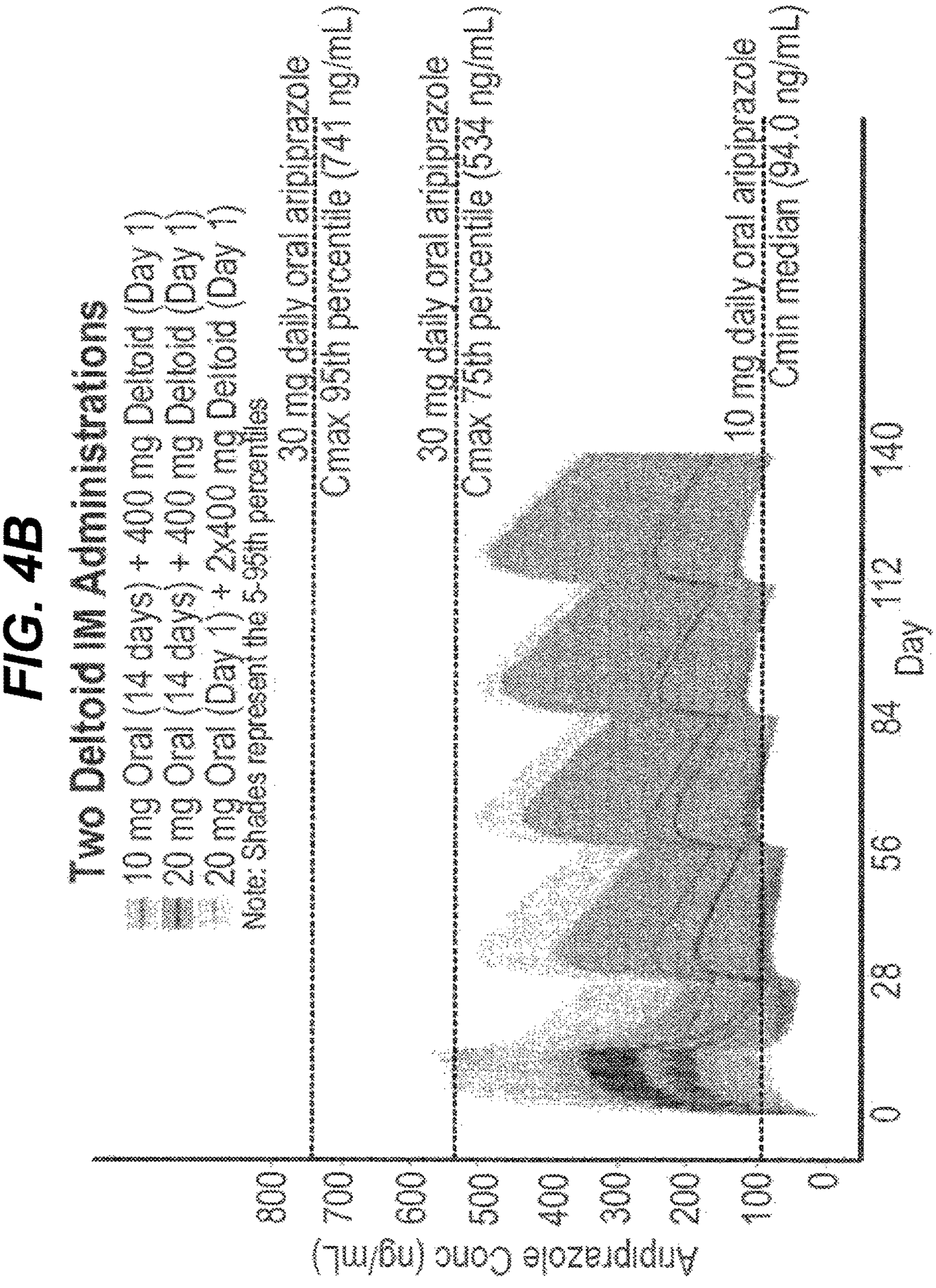
Figure 4C:
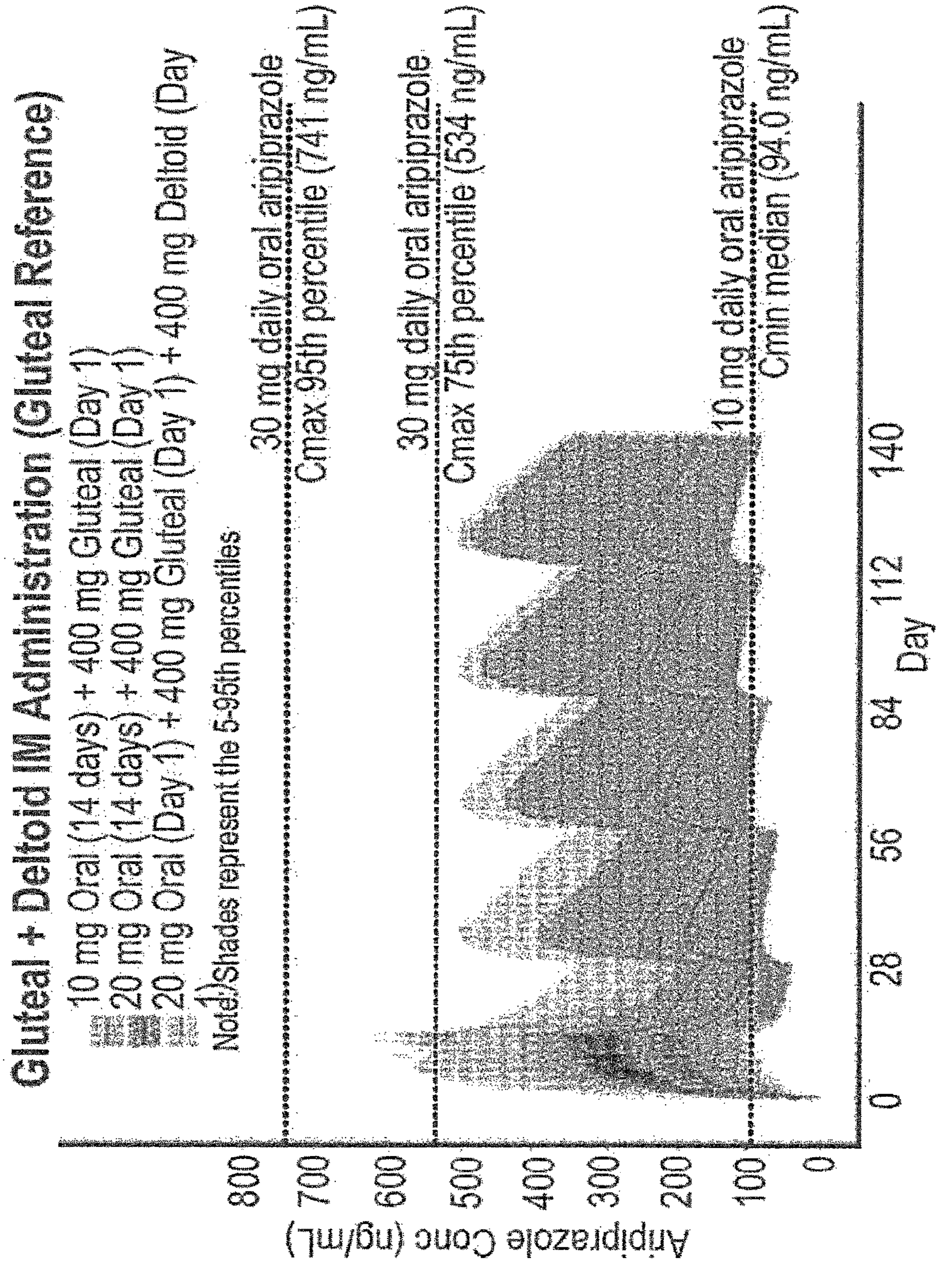
Figure 4D:
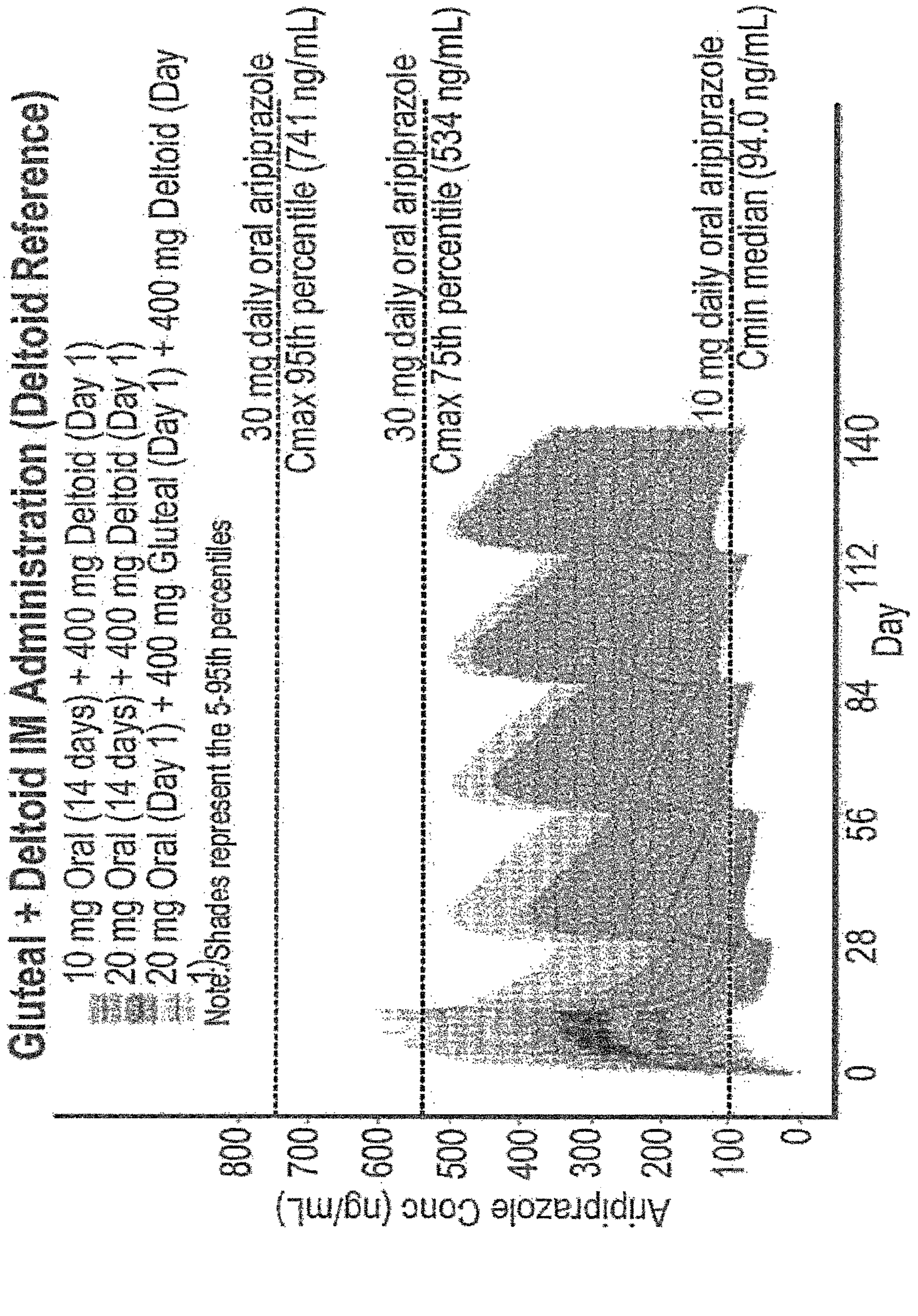

As used herein, "a" or "an" entity refers to one or more of that entity, e.g., "a compound" refers to one or more compounds or at least one compound unless stated otherwise. As such, the terms "a" (or "an"), "one or more", and "at least one" are used interchangeably herein.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%.

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art. In some embodiments, the presently disclosed methods or depot formulations can be used to treat schizophrenia and bipolar I disorder, as maintenance monotherapy. In further embodiments, the presently disclosed methods or depot formulations can be used to treat schizophrenia, acute treatment of manic and mixed episodes associated with Bipolar I disorder, major depressive disorder (MDD), irritability with Autistic Disorder, and Tourette's disorder.

As used herein, a "mammal" refers to domesticated animals (e.g., dogs, cats, and horses) and humans. In some embodiments, the mammal is a human.

EMBODIMENTS

Without limitation, some embodiments of the disclosure include:

1. A method of dose initiation for an aripiprazole treatment to a patient in need thereof comprising:
   administering two, separate injections of an aripiprazole intramuscular (IM) depot formulation, wherein each injection comprises from about 10 mg to about 500 mg of aripiprazole to the patient at separate gluteal and/or deltoid injection sites, and a single dose of oral aripiprazole, wherein the step of administering occurs on a first day of the treatment.

2. The method according to embodiment 1, wherein each of the two, separate injections comprises 400 mg of aripiprazole.

3. The method according to embodiment 1 or 2, further comprising after the first day of treatment, administering a single monthly, maintenance injection of the aripiprazole IM depot formulation.

4. The method according to embodiment 3, wherein the single monthly, maintenance injection is chosen from about 300 mg and about 400 mg of the aripiprazole IM depot formulation.

5. The method according to embodiment 3, wherein when the patient is a CYP2D6 poor metabolizer or is taking concomitant CYP3A4 inhibitors or CYP2D6 inhibitors for greater than 14 days, the single monthly, maintenance injection is chosen from 160 mg and 200 mg of the aripiprazole IM depot formulation.

6. The method according to any one of embodiments 1 to 5, wherein the two, separate injections of the aripiprazole IM depot formulation are administered at separate gluteal injection sites of the patient.

7. The method according to any one of embodiments 1 to 5, wherein the two, separate injections of the aripiprazole IM depot formulation are administered at gluteal and deltoid injection sites of the patient.

8. The method according to any one of embodiments 1 to 5, wherein the two, separate injections of the aripiprazole IM depot formulation are administered at separate deltoid injection sites of the patient.

9. The method according to any one of embodiments 1 to 8, wherein the patient has schizophrenia.

10. The method according to any one of embodiments 1 to 8, wherein the patient has bipolar I disorder.

11. The method according to any one of embodiments 1 to 10, wherein the single dose of oral aripiprazole ranges from about 2 mg to about 30 mg of aripiprazole.

12. The method according to embodiment 11, wherein the single dose of oral aripiprazole ranges from about 10 mg to about 30 mg.

13. The method according to embodiment 11, wherein the single dose of oral aripiprazole is 20 mg.

14. The method according to embodiment 11, wherein the single dose of oral aripiprazole is 10 mg.

15. The method according to embodiment 1, wherein when the patient is a CY2D6 poor metabolizer, each of the two, separate injections comprises about 300 mg of aripiprazole and the single dose of oral aripiprazole is about 20 mg.

The present disclosure is directed to an alternative initiation regimen of two, separate administrations of an aripiprazole intramuscular (IM) depot formulation together with a shorter oral overlap. For example, simulations of an alternative initiation regimen of two 400 mg injections of an aripiprazole intramuscular (IM) depot formulation (e.g., Abilify Maintena(R)) at separate gluteal and/or deltoid injection sites together with a single 20 mg dose of oral aripiprazole on the first day of treatment is shown to be sufficient and the alternative initiation regimen may be an additional option for initiation of, e.g., Abilify Maintena(R).

Aripiprazole is 7-[4-[4-(2,3-dichlorophenyl)-1-piperazinyl]butoxy]-3,4-dihydrocarbostyril. The empirical formula is $C_{23}H_{27}Cl_2N_3O_2$ and its molecular weight is 448.38. The chemical structure is:

[Chem.1]

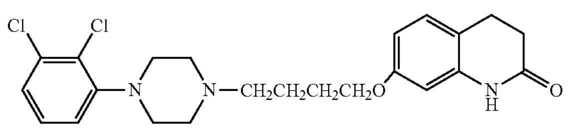

As used herein, reference to aripiprazole is to aripiprazole or a salt thereof, the crystalline form of aripiprazole or a salt thereof. Aripiprazole or a salt thereof may be in a monohydrate form (aripiprazole hydrate A) or in various anhydrous forms, which are known to exist in the form of anhydrous crystal B, anhydrous crystal C, anhydrous crystal D, anhydrous crystal E, anhydrous crystal F, and anhydrous crystal G. All of these crystalline forms may be used as aripiprazole or a salt thereof in the injectable preparation of the present disclosure and further for example, aripiprazole is a monohydrate form.

A pharmaceutical composition comprising aripiprazole is known as an antipsychotic useful for the treatment of schizophrenia and bipolar disorder I.

Aripiprazole Traditional Dosing Regimen

The aripiprazole traditional dosing regimen includes a recommended starting and maintenance dose of Abilify Maintena(R) that is 300 mg or 400 mg monthly (no sooner than 26 days after the previous injection). For patients who have never taken aripiprazole, the patient establishes tolerability with oral aripiprazole prior to initiating treatment with Abilify Maintena(R). Due to the half-life of oral aripiprazole, it may take up to 2 weeks to fully assess tolerability.

After the first Abilify Maintena(R) injection, administer oral aripiprazole (10 mg to 20 mg) for 14 consecutive days to achieve therapeutic aripiprazole concentrations during initiation of therapy. For patients already stable on another oral antipsychotic (and known to tolerate aripiprazole), after the first Abilify Maintena(R) injection, continue treatment with the antipsychotic for 14 consecutive days to maintain therapeutic antipsychotic concentrations during initiation of therapy.

If there are adverse reactions with the 400-mg dosage, one can consider reducing the dosage to 300 mg once monthly.

As such, the currently approved initiation regimen consists of a single IM injection of aripiprazole intramuscular depot formulation together with daily oral tablet administration of aripiprazole (10 to 20 mg) for 14 consecutive days.

Reference herein to an aripiprazole intramuscular depot formulation refers to Abilify Maintena(R) (aripiprazole), prescribing information for extended-release injectable suspension, for intramuscular use, initial US approval: 2002, revised: 6/2020.

Aripiprazole Alternative Dosing Regimen

The present disclosure is directed to an alternative initiation regimen or dose initiation comprising administering two, separate about 100 mg to about 500 mg injections of aripiprazole intramuscular depot formulation (Abilify Maintena(R)) at separate gluteal and/or deltoid injection sites together with a single oral aripiprazole dose on the first day of treatment. The single oral dose aripiprazole ranges from about 2 mg to about 30 mg; for example, the single oral dose aripiprazole ranges from about 10 mg to about 30 mg. This alternative initiation regimen provides an option for the first, or initiation, dose of aripiprazole intramuscular depot formulation. Maintenance dosing remains unchanged; for example, maintenance dose follows with single monthly injections thereafter of 400 mg or 300 mg of aripiprazole IM depot formulation. As with the traditional dose initiation regimen, the alternative initiation regimen is applicable to both the deltoid and gluteal administration sites.

The present disclosure utilizes two, separate aripiprazole intramuscular depot formulation injections with a dose ranging from about 100 to about 500 mg of aripiprazole. For example, the methods of the present disclosure administer two, separate 400 mg injections of an aripiprazole intramuscular (IM) depot formulation to the patient at separate gluteal and/or deltoid injection sites with administration occurring on a first day of the treatment. In some embodiments, the two, separate injections of the aripiprazole IM depot formulation are administered at separate gluteal injection sites or at separate deltoid sites of the patient. In a further embodiment, the two, separate injections of the aripiprazole IM depot formulation are administered at a gluteal and a deltoid injection site of the patient. Further, the patient has schizophrenia and for example, the patient has bipolar I disorder.

The rationale for the selection of the alternative initiation regimen dose is based on simulations from a population pharmacokinetic(s) (popPK) model. A range of dose initiation regimens were considered to shorten the length of oral dosing overlap with the first IM depot injection while maintaining median concentrations within the previously defined therapeutic window and similar to those of the currently approved dose initiation regimen (i.e., median, 25th to 75th, and 5th to 95th percentile of concentration). Based on the results of the simulations, the recommended dose for the alternative initiation regimen ranges from about 100 mg to about 500 mg and in some embodiments, is, e.g., two 400 mg injections of the aripiprazole intramuscular depot formulation at separate gluteal and/or deltoid injection sites together with a single dose of oral aripiprazole on the first day of treatment, for example, the single dose of oral aripiprazole ranges from about 2 mg to 30 mg of aripiprazole and for example, is a single 20 mg dose of oral aripiprazole.

Clinical Pharmacology Studies

The objective of the clinical pharmacology studies was to establish a two-injection start regimen for the long-acting injectable aripiprazole once-monthly to obviate the need for 14-day oral aripiprazole supplementation during treatment initial using a PK modeling and simulation approach.

Methods

A previously developed popPK model (Food and Drug Administration: Center for Drug Evaluation and Research, Aripiprazole IM Depot Formulation: Clinical Pharmacology and Biopharmaceutics Review (Application No. 202971s000) 2012)) which could adequately characterize aripiprazole PK following oral administration and gluteal IM depot injections was expanded to include the deltoid site of injection. The final model was developed using PK data from 7 clinical trials following oral administration and IM depot injections (both gluteal and deltoid muscles). A total of 8,214 aripiprazole concentrations (16% oral, 65% gluteal, 16% deltoid, and 3% triceps or thigh administration) from 817 subjects were included in the final analysis dataset. The predictive performance of the final model was assessed by prediction-corrected visual predictive checks (pc VPCs).

The final popPK model was used to simulate and evaluate a range of dose initiation regimens with shorter oral overlap following the first IM depot injection to identify a regimen that: (1) remains within a previously establish therapeutic window corresponding to the lower bound of the simulated median minimum aripiprazole concentrations at steady state (Cmax,ss) following daily administration of 10 mg oral aripiprazole (94.0 ng/mL) and the $95^{th}$ percentile of maximum aripiprazole concentrations at steady state (Cmax,ss) following daily administration of the highest approved oral aripiprazole dose of 30 mg (741 ng/mL); and (2) results in plasma concentrations similar (i.e., median, $25^{th}$ to $75^{th}$, and $5^{th}$ to $95^{th}$ percentile of concentration) to that of the currently approved one-injection start initiation regimen (one 400 mg injection of aripiprazole once-monthly together with 14 days of oral aripiprazole [10 to 20 mg]).

A summary of the popPK modeling and simulation to support the alternative initiation regimen is provided, under "popPK Modeling" section header below. Simulations of aripiprazole plasma concentration time profiles following administration of the alternative initiation regimen to subjects without and with prior stabilization on oral aripiprazole (under "Alternative Initiation Regimen Without Prior Oral Aripiprazole Stabilization" and "Alternative Initiation Regimen With Prior Oral Aripiprazole Stabilization" section headers below), to extensive or poor cytochrome P450 2D6 (CYP2D6) metabolizers (under "Subjects who are CYP2D6 Poor Metabolizers" section header below), and in scenarios following missed maintenance doses are also presented in this module (under "Missed Maintenance IM Depot Dose" section header below).

Aripiprazole Oral Formulation

Aripiprazole is a psychotropic drug that is available as an oral (aripiprazole) tablet. In some embodiments, oral tablets of aripiprazole are available in, e.g., 2 mg, 5 mg, 10 mg, 15 mg, 20 mg, and 30 mg strengths. Inactive ingredients in oral tablets, e.g., include cornstarch, hydroxypropyl cellulose, lactose monohydrate, magnesium stearate, and microcrystalline cellulose. Colorants can include, e.g., ferric oxide (yellow or red) and FD&C Blue No. 2 Aluminum Lake.

Aripiprazole is well absorbed after administration of a tablet, with peak plasma concentrations occurring, e.g., within 3 hours to 5 hours; the absolute oral bioavailability of the tablet formulation is about 87%. Oral tablets of aripiprazole can be administered with or without food. For example, administration of a 15 mg oral tablet of aripiprazole with a standard high-fat meal did not significantly affect the Cmax or AUC of aripiprazole or its active metabolite, dehydro-aripiprazole, but delayed Tmax by 3 hours for aripiprazole and 12 hours for dehydro-aripiprazole.

Aripiprazole is metabolized primarily by three biotransformation pathways: dehydrogenation, hydroxylation, and N-dealkylation. Based on in vitro studies, CYP3A4 and CYP2D6 enzymes are responsible for dehydrogenation and hydroxylation of aripiprazole, and N-dealkylation is catalyzed by CYP3A4. Aripiprazole is the predominant drug moiety in the systemic circulation. At steady-state, dehydro-aripiprazole, the active metabolite, represents about 40% of aripiprazole AUC in plasma.

Following a single oral dose of [14C]-labeled aripiprazole, approximately 25% and 55% of the administered radioactivity was recovered in the urine and feces, respectively. Less than 1% of unchanged aripiprazole was excreted in the urine and approximately 18% of the oral dose was recovered unchanged in the feces.

The present disclosure utilizes an oral tablet of aripiprazole at a single oral dose chosen from 2 mg to 30 mg, such as single oral doses of 2 mg, 5 mg, 10 mg, 15 mg, 20 mg, and 30 mg of aripiprazole. In some embodiments, the single oral dose ranges from about 10 mg to about 30 mg of aripiprazole, such as about 20 mg of aripiprazole. In some embodiments, the single oral dose is chosen from 10 mg and 20 mg of aripiprazole. In further embodiments, the single oral dose is 20 mg of aripiprazole.

Aripiprazole Intramuscular Depot Formulation

In some embodiments, aripiprazole intramuscular depot formulation comprises aripiprazole monohydrate; aripiprazole monohydrate is 7-[4-[4-(2,3-dichlorophenyl)-1-piperazinyl]butoxy]-3,4 dihydrocarbostyril monohydrate. The empirical formula is $C_{23}H_{27}Cl_2N_3O_2 \cdot H_2O$ and its molecular weight is 466.40. The chemical structure is:

[Chem.2]

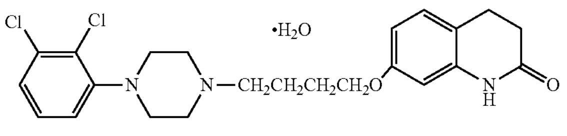

For example, in some embodiments, aripiprazole intramuscular (IM) depot formulation is an extended-release injectable suspension in 400-mg or 300-mg strength in pre-filled dual chamber syringes and 400-mg or 300-mg strength vials. The labeled strengths are calculated based on the anhydrous form (aripiprazole). In some embodiments, inactive ingredients (per administered dose) for 400-mg and 300-mg strength products, respectively, include carboxymethyl cellulose sodium (16.64 mg and 12.48 mg), mannitol (83.2 mg and 62.4 mg), sodium phosphate monobasic monohydrate (1.48 mg and 1.11 mg) and sodium hydroxide (pH adjuster). In further embodiments, the extended-release injectable suspension in 400-mg or 300-mg strength in pre-filled dual chamber syringes and 400-mg or 300-mg strength vials can be used to make dosage adjustments; that is, in patents who arc CYP2D6 poor metabolizers and in patents taking concomitant CYP3A4 inhibitors or CYP2D6 inhibitors. Dosage adjustments for 200 mg and 160 mg can be obtained by using the 300-mg or 400-mg strength vials for intramuscular deltoid or gluteal injection for patients taking CYP2D6 inhibitors, CYP3A4 inhibitors, or CYP3A4 for greater than 14 days. The presently disclosed aripiprazole IM depot formulation, Ability Maintena(R), for suspension in an extended-release form is described in U.S. Pat. Nos. 7,807,680, 8,030,313, 8,338,427, 8,338,428, 8,399,469, 8,722,679, 8,759,351, 8,993,761, 9,089,567, and 10,525,057; all of which are incorporated herein by reference in their entirety.

In some embodiments, the activity of the aripiprazole intramuscular depot formulation is presumably primarily due to the parent drug, aripiprazole, and to a lesser extent, to its major metabolite, dehydro-aripiprazole, which has been shown to have affinities for D2 receptors similar to the parent drug and represents about 29% of the parent drug exposure in plasma.

Aripiprazole absorption into the systemic circulation is slow and prolonged following intramuscular injection due to low solubility of aripiprazole particles. Following a single-dose administration of the aripiprazole intramuscular depot formulation in the deltoid and gluteal muscle, the extent of absorption (AUCt, AUC∞) of aripiprazole was similar for both injection sites, but the rate of absorption (Cmax) was 31% higher following administration to the deltoid compared to the gluteal site. However, at steady state, AUC and Cmax were similar for both sites of injection. Following multiple intramuscular doses, the plasma concentrations of aripiprazole gradually rise to maximum plasma concentrations at a median Tmax of about 5-7 days for the gluteal muscle and about 4 days for the deltoid muscle. After gluteal administration, the mean apparent aripiprazole terminal elimination half-life was about 29.9 days and about 46.5 days after multiple injections for every 4-week injection of the aripiprazole intramuscular depot formulation 300 mg and 400 mg, respectively. Steady state concentrations for the typical subject were attained by the fourth dose for both sites of administration. Approximate dose-proportional increases in aripiprazole and dehydro-aripiprazole exposure were observed after every four-week of the aripiprazole intramuscular depot formulation injections of 300 mg and 400 mg.

Elimination of aripiprazole is mainly through hepatic metabolism involving two P450 isozymes, CYP2D6 and CYP3A4. Aripiprazole is not a substrate of CYP1A1, CYP1A2, CYP2A6, CYP2B6, CYP2C8, CYP2C9, CYP2C19, or CYP2E1 enzymes. Aripiprazole also does not undergo direct glucuronidation.

The present disclosure utilizes two, separate aripiprazole intramuscular depot formulation injections with a dose ranging from about 100 mg to about 500 mg of aripiprazole, and further for example, each of the two-aripiprazole intramuscular depot formulation injections comprise a dose of 300 mg or 400 mg of aripiprazole. For example, the methods of the present disclosure administer two, separate 300 mg or 400 mg injections of an aripiprazole intramuscular (IM) depot formulation to the patient at separate gluteal and/or deltoid injection sites with administration occurring on a first day of the treatment. In some embodiments, the two, separate injections of the aripiprazole IM depot formulation are administered at separate gluteal injection sites or at separate deltoid sites of the patient. In a further embodiment, the two, separate injections of the aripiprazole IM depot formulation are administered at a gluteal and deltoid injection site of the patient. Further, the patient has schizophrenia and for example, the patient has bipolar I disorder.

EXAMPLES

Figure 10:
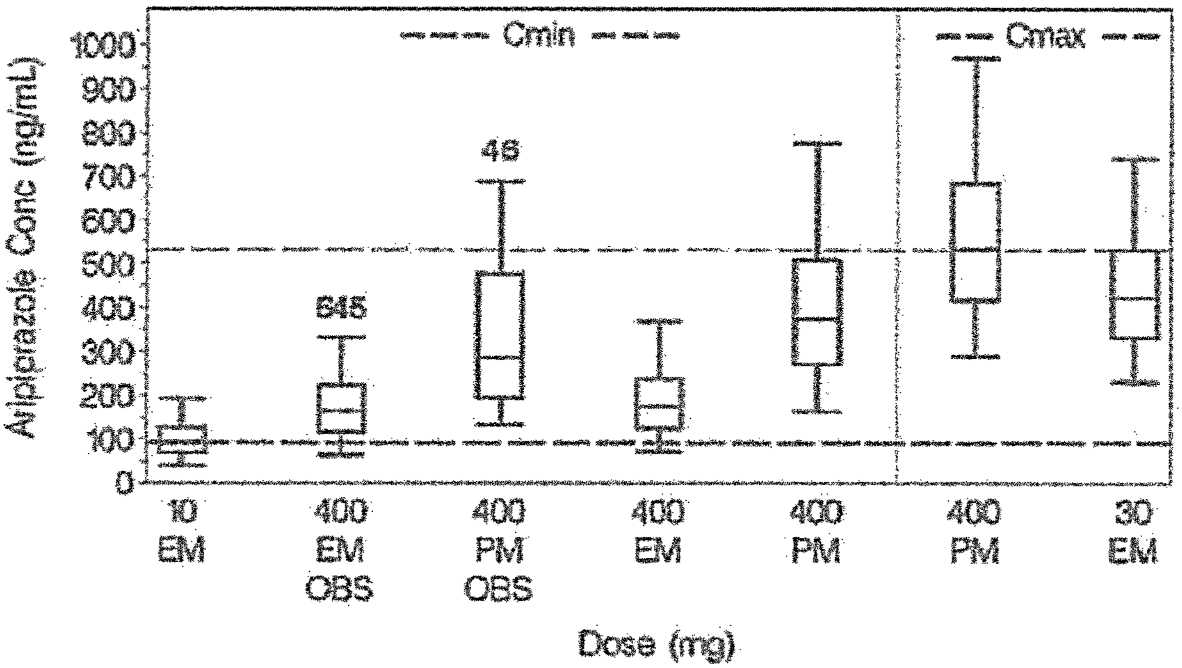
FIG. 10 illustrates simulated and observed aripiprazole concentrations following oral and gluteal intramuscular depot administration of aripiprazole in support of the definition of the therapeutic window.

Therapeutic Window and Aripiprazole Plasma Concentrations During Dose Initiation with Alternative Initiation Regimen The previously proposed therapeutic window corresponding to the lower bound of the simulated median minimum aripiprazole concentrations at steady state (Cmin,ss) following daily administration of 10 mg oral aripiprazole (94.0 ng/ml) and a conservative upper bound of the simulated 75th percentile of maximum aripiprazole concentrations at steady state (Cmax,ss) following daily administration of the highest approved oral aripiprazole dose of 30 mg (534 ng/mL) is provided in FIG. 10. The statistics related to the simulations in this disclosure are presented with median, 25th to 75th and 5th to 95th percentile of concentration. Thus, for head to head comparison of these simulations with the previously proposed therapeutic window (FIG. 10), a horizontal reference line denoting the 95th percentile of the previously simulated Cmax,ss concentrations following daily administration of 30 mg oral aripiprazole (741 ng/mL) is added to simulations provided in this disclosure.

Figure 13:
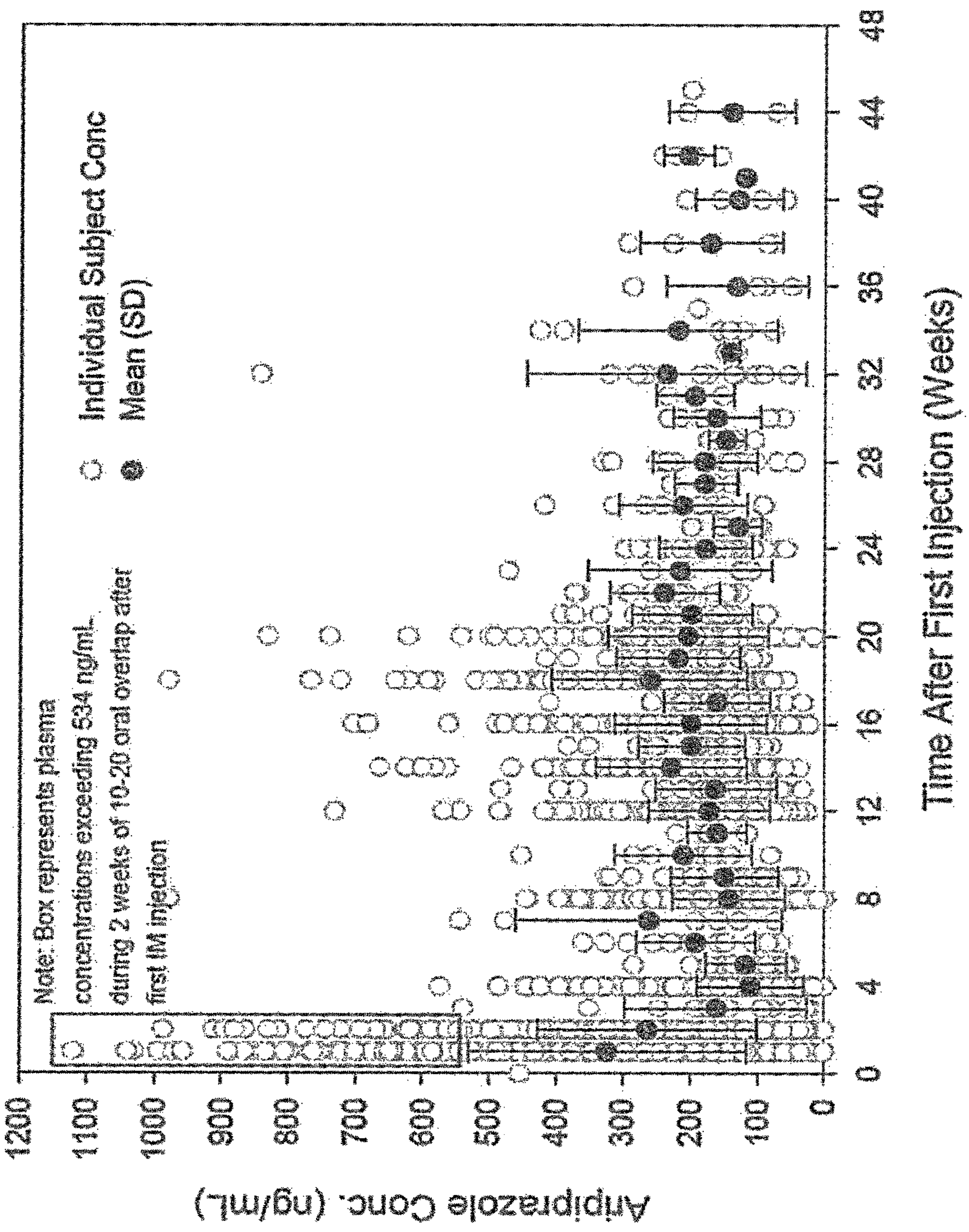
FIG. 13 illustrates observed aripiprazole plasma concentrations by week after first intramuscular depot injection. The box represents plasma concentrations exceeding 534 ng/mL during 2 weeks of 10-20 oral overlap after first IM injection.

Based on simulations provided under the "Simulation Results" header found below, aripiprazole concentrations during dose initiation could reach the 95th percentile of the previously simulated Cmax,ss concentrations following daily administration of 30 mg oral aripiprazole (741 ng/ml), thus the following supportive information in lieu of clinical data is provided:

- Observed PK and safety data from a subset of subjects in this trial with aripiprazole plasma concentrations that fell within the 5th to 95th percentile of simulated concentrations following administration of the proposed alternative initiation regimen was evaluated and is provided under the "Comparison and Analyses of Results Across Trials" header below. Overall, the safety profile of these subjects was in accordance with the known safety profile of Abilify Maintena(R).
- Aripiprazole concentrations exceeding both the 75th and 95th percentile of simulated 30 mg oral Cmax,ss were observed and well tolerated in a previously submitted phase 3 safety and efficacy trial (clinicaltrials.gov identifier: NCT00705783, entitled "Intramuscular Depot Formulation of Aripiprazole as Maintenance Treatment in Patients with Schizophrenia (ASPIRE)."). Plasma concentrations exceeding these levels during dose initiation are highlighted in FIG. 13. In FIG. 13, SD equals standard deviation.

Summary of Results of Individual Studies

A population PK analysis was conducted to expand the previously submitted popPK model to incorporate the deltoid site of injection and perform simulations to examine predicted plasma concentrations following administration of the alternative initiation regimen at both deltoid and gluteal sites. A summary of the final combined popPK model is provided under the "popPK" heading below. A summary of the results of a single ascending dose phase 1 trial to determine the PK, safety and tolerability following gluteal administration of a single high dose formulation of aripiprazole LAI that is provided under the "popPK" heading below.

popPK Modeling: Population Pharmacokinetic Analysis of Aripiprazole Following Oral Administration and Intra-Muscular Injection in the Gluteal or Deltoid Muscle in Adult Subjects A total of 8214 aripiprazole concentrations (16% oral, 65% gluteal, 16% deltoid, and 3% triceps or thigh administration) from 817 subjects were included in a final combined analysis dataset. Pharmacokinetic data included in this analysis consisted of data included from a previous popPK report as well as aripiprazole concentrations following deltoid or gluteal injections from 2 additional trials conducted to support addition of the deltoid muscle as a site of administration.

The model was a 3-compartment model with sigmoid absorption for oral administration (Ka), and 1st order absorption for IM (mainly gluteal) administration (IMKa).

The final combined model included the deltoid injection site into the previously developed model by adding a deltoid depot compartment with a separate absorption rate constant (DKa) to the original model. No further structural change or covariate analysis was conducted. A diagram of the structure of the final combined model is presented in FIG. 1, with updates to the original model to incorporate the deltoid site of injection shown in broken lines. In FIG. 1, the following abbreviations are used: CMT=compartment; DKa=deltoid IM 1st order absorption rate constant; Frelative=relative bioavailability; IMKa=gluteal IM 1st order absorption rate constant; Ka=oral 1st order absorption rate constant; R1=rate of dose into oral absorption compartment; Vc=apparent central volume of distribution; Vp1=volume of distribution in Peripheral compartment 1; Vp2=volume of distribution in Peripheral compartment 2; Q1=inter-compartmental clearance 1; Q2=inter-compartmental clearance 2. The final popPK model was a linear 3-compartment PK model, which utilizes sigmoid absorption for oral administration and separate 1st order absorption for the gluteal and deltoid IM injections of aripiprazole once-monthly.

All population PK parameters were fixed to the values estimated in the original model for oral and gluteal administration except for DKa, which was estimated using data following deltoid administration. The inter-individual variability (IIV) for the oral absorption rate constant (Ka) was fixed to the value estimated in the original model, while IIV for clearance (CL), central volume of distribution (Vc), and the first order absorption rate constants following IM injections (IMKa and DKa) were estimated or re-estimated using the final combined analysis dataset.

It was assumed that the covariate effect remained the same as the original model, and that the gender and body mass index (BMI) effect on IMKa, estimated from data following IM injection in gluteus maximus mainly, is also present for the deltoid injection. No additional covariate analysis was performed. Parameter definition and values of the final combined model are presented in Table 1 below:

TABLE 1

Parameter Estimates of the Final Combined Model

| Parameter | Unit | Definition | Estimate | RSE % | Shrinkage % |
|---|---|---|---|---|---|
| R1 | mg/hr | Rate of dose into oral absorption compartment | 9.33 Fixed | | |
| Ka | 1/hr | Oral 1st order absorption rate constant | 0.540 Fixed | | |
| CL | L/hr | Apparent clearance for subjects who are not poor CYP2D6 metabolizers | 3.71 Fixed | | |
| CLpm | Lhr | Apparent clearance for subjects who are poor CYP2D6 metabolizers | 1.88 Fixed | | |
| CL_INH2D6 | — | Proportional change in CL in presence of a strong CYP2D6 inhibitor | −0.511 Fixed | | |
| CL_INH3A4 | — | Proportional change in CL in presence of a strong CYP3A4 inhibitor | −0.237 Fixed | | |
| Vc | L | Apparent central volume of distribution | 93.4 Fixed | | |
| Q1 | L/hr | Inter-compartmental clearance 1 | 0.591 Fixed | | |
| Vp1 | L | Volume of distribution in Peripheral compartment 1 | 118 Fixed | | |
| Q2 | L/hr | Inter-compartmental clearance 2 | 28.8 Fixed | | |

TABLE 1-continued

| Parameter Estimates of the Final Combined Model | | | | | |
|---|---|---|---|---|---|
| Parameter | Unit | Definition | Estimate | RSE % | Shrinkage % |
| Vp2 | L | Volume of distribution in Peripheral compartment 2 | 134 Fixed | | |
| IMKa | 1/hr | Gluteal IM 1st order absorption safe constant | 0.000904 Fixed | | |
| DKa | 1/hr | Deltoid IM 1st order absorption rate constant | 0.000776 | 6.2% | |
| IM Ka_BMI | — | Effect of BMI on IH Ka: power for (BMI/28) | −0.975 Fixed | | |
| IM Ka_male | — | Proportional shift of IM Ka for males | 0.346 Fixed | | |
| F relative | — | Relative siosvallability for IM Depot | 1.48 Fixed | | |
| Radom Effect Inter-Individual Variability (CV %) | | | | | |
| Ka | — | IIV on oral Ka | 0.434 (65.9%) Fixed | — | 77% |
| CL and CLpm | — | IIV on Apparent clearance for all subjects | 0.153 (39.1%) | 6.1% | 8% |
| Vc | — | IIV on Vc | 2.18 (148%). | 2.5% | 44% |
| IMKa | — | IIV on gluteal IM Ka | 0.359 (60.0%) | 7.7% | 24% |
| DKa | — | IIV on deltoid IM Ka | 0.237 (48.9%) | 24.4% | 74% |
| Residual Variability (% CV) | | | | | |
| Phase 1 | — | Proportional residual error for phase 1 data | 0.0693 (26.3%) | — | — |
| Phase 3 | — | Proportional residual error for phase 3 data | 0.0600 (24.5%) | — | — |
| Minimum Value of Objective Function: 64759 | | | | | |

From Table 1, it is noted that % CV is the percent coefficient of variation and RSE is standard error relative to the mean.

The predictive performance of the final combined model was assessed by prediction-corrected visual predictive checks (pcVPCs). The pcVPCs of the final combined population PK model for deltoid and gluteal sites of administration following the first and the fifth monthly administrations are presented in FIGS. 2A-2D. In FIGS. 2A-2D, the following abbreviations are used: CI=confidence interval; and the visual predictive check following the 1st gluteal injection includes PK data from subjects co-administered with oral aripiprazole. Overall, the pcVPCs showed good predictive performance of the final combined model for the deltoid and gluteal sites of administration as the distributions of the observed data are comparable with the 5th to 95th percentile of concentrations of the model-based simulation. Overall, peVPCs confirmed the variability seen in the observed PK data could be adequately described by the final popPK model, as the distributions of the observed data are comparable with the 90% prediction intervals of the model-based simulation following single and multiple administrations in the deltoid and gluteal sites.

Simulation Results

The final combined model was utilized to simulate aripiprazole plasma concentration-time profiles following oral, gluteal, and/or deltoid administration of aripiprazole. To compare simulated PK profiles, a virtual population consisting of 817 subjects with similar demographic characteristics to the subjects enrolled in the clinical trials in the final analysis dataset (provided under "popPK Model") was used to ensure only the dosing regimen changed across simulations. Individual PK parameters for subjects in the final analysis dataset (all assigned as CYP2D6 extensive metabolizers (EM) except for simulation of CYP2D6 poor metabolizers [PM] subjects) were generated from the final combined PK model and its final parameter estimates. Individual PK profiles following oral, gluteal, and deltoid administration of aripiprazole were simulated using a 2-hour sampling interval for 24 hours post the preceding oral dose and every 24-hour sampling post the preceding IM Depot dose. A full listing of all simulations performed is provided in FIGS. 3A-3C.

Alternative Initiation Regimen Without Prior Oral Aripiprazole Stabilization Several scenarios for dose initiation were simulated to assess the time to achieve concentrations within the therapeutic window as provided above under the heading entitled "Therapeutic Window and Aripiprazole Plasma Concentrations During Dose Initiation with Alternative Initiation Regimen." The median and 5th to 95th percentile of concentration of simulated aripiprazole plasma PK profiles for the currently approved initiation regimen (400 mg with 14 days of 10 to 20 mg oral dosing) and the alternative initiation regimen (2×400 mg with 1 day of 20 mg oral dosing) administered as two separate injections in the gluteal and/or deltoid sites are shown in FIGS. 4A-4D. In FIGS. 4A-4D, approved initiation regimen was 10 to 20 mg oral (14 days) and 400 mg IM depot (day 1).

Based on the simulations, in FIGS. 4A-4D, the median and 5th to 95th percentile of concentration of the aripiprazole PK profile following administration of the proposed alternative initiation regimen is comparable to the approved initiation regimen of 400 mg aripiprazole IM on Day 1+10 mg to 20 mg oral aripiprazole for 14 days, for example:

Median aripiprazole PK profiles following the alternative initiation regimen reach therapeutic levels (10 mg daily aripiprazole Cmin,ss of 94.0 ng/ml) on the first day and remain above the lower threshold of the therapeutic window thereafter.

The 95th percentile of simulated concentrations following the proposed alternative initiation regimen are comparable to, or lower than, the 95th percentile of the currently approved regimen and within the upper bound of the therapeutic window, as discussed above.

Plasma concentrations for all regimens exceed the previously used conservative upper bound of the 75th percentile of simulated Cmax,ss following daily administration of 541 ng/mL but remain below the 95th percentile of the simulated 30 mg oral Cmax,ss (741 ng/ml).

The alternative initiation regimen has no impact on steady state maintenance concentration.

Alternative Initiation Regimen With Prior Oral Aripiprazole Stabilization

Figure 5A:
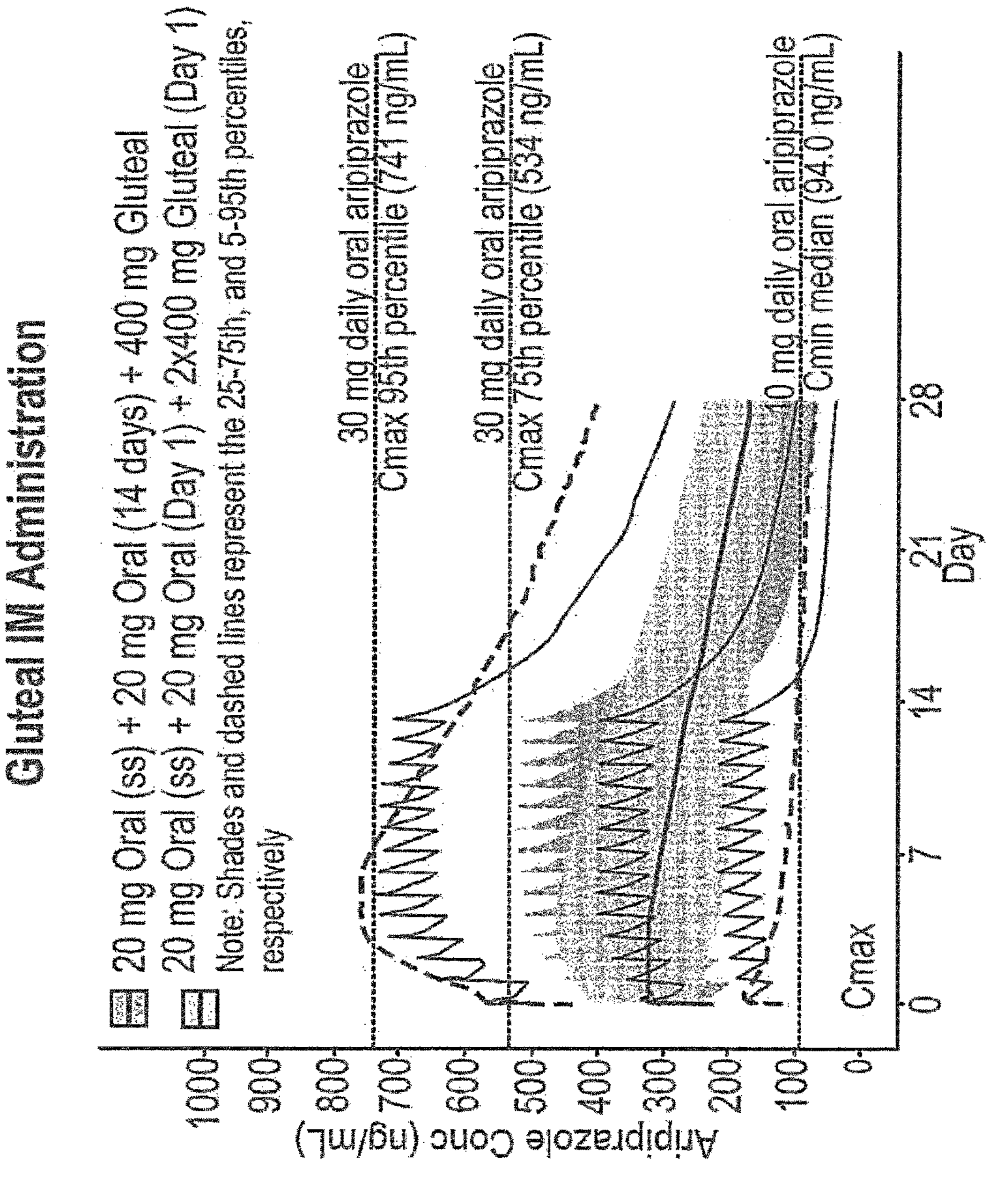
FIGS. 5A and 5B are diagrams of simulated median, $5^{th}$, $25^{th}$ to $75^{th}$, and $95^{th}$ percentiles of pharmacokinetic profiles following administration of the current or alternative initiation regimen to subjects already stabilized on 20 mg oral aripiprazole. The shades and dashed lines represent the $5^{th}$, $25^{th}$-$75^{th}$, and $95^{th}$ percentiles, respectively.
Figure 5B:
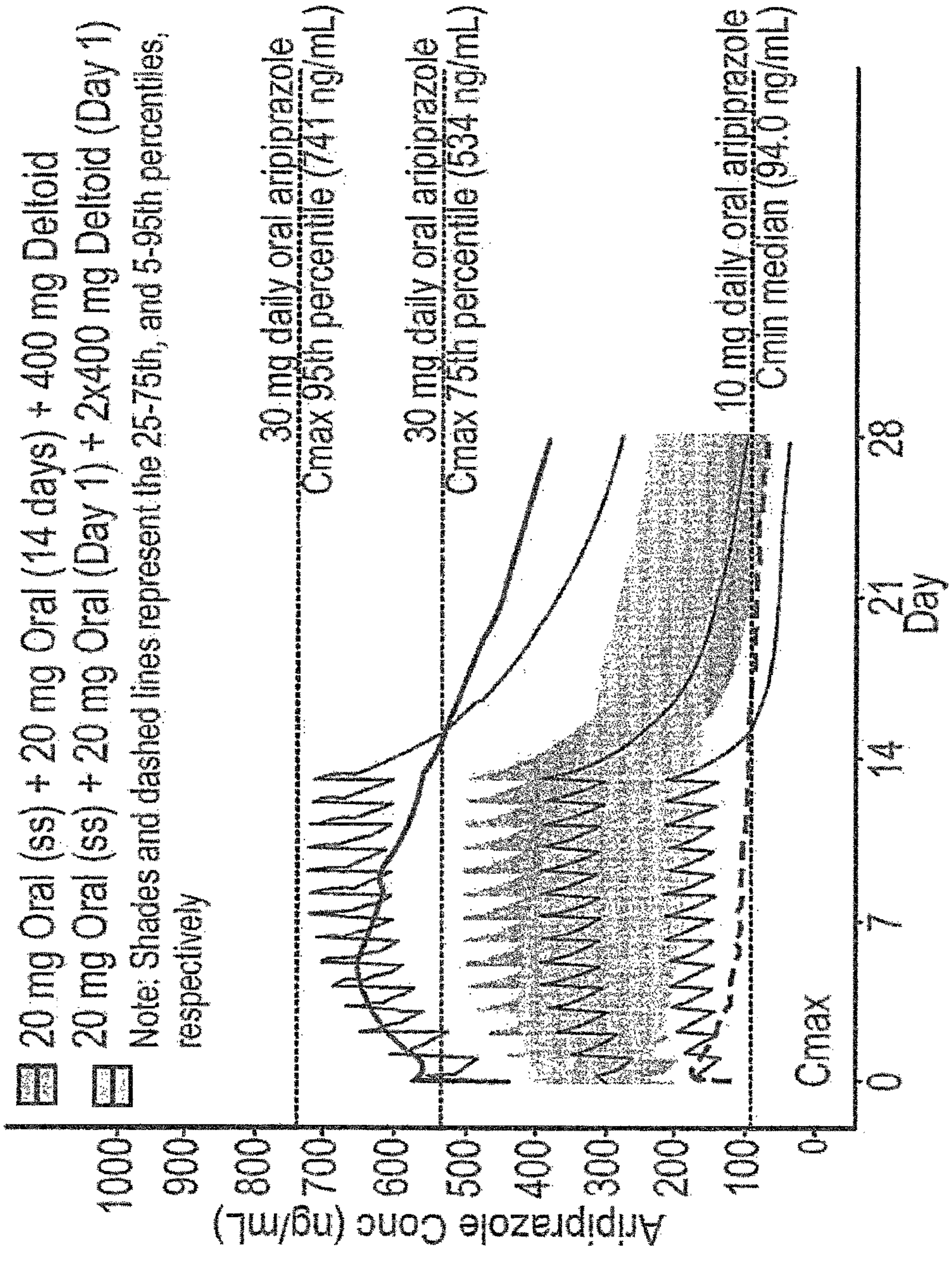

In the approved label for Abilify Maintena(R), the first dose is administered with concomitant oral aripiprazole (10 to 20 mg) for 14 consecutive days to adult patients stabilized with oral aripiprazole. Thus, simulations were performed to predict and compare plasma concentrations during the 28 days following administration of the currently approved and the alternative initiation regimen to patients stabilized with 20 mg aripiprazole, which is the highest typical oral dose a patient would be receiving prior to initiating treatment with IM depot of aripirazole. The median, 5th, 25th to 75th, and 95th percentile of simulated aripiprazole plasma PK profiles for the currently approved and the alternative initiation regimen administered as two separate injections in the gluteal or deltoid sites of subjects with prior stabilization on an oral aripiprazole dose of 20 mg are presented in FIGS. 5A and 5B. In FIGS. 5A and 5B, the approved initiation regimen was 10 to 20 mg oral (14 days) and 400 mg IM depot (Day 1). The starting concentration at time zero is the average concentration at steady state for subjects stabilized on 20 mg oral aripiprazole.

Based on the simulations, the median and 5th to 95th percentile of concentration of the aripiprazole PK profile following administration of the alternative initiation regimen is comparable to the approved initiation regimen when administered to subjects already stabilized on 20 mg oral aripiprazole:

The 95th percentile of simulated concentrations following the alternative initiation regimen are comparable to, or lower than, the 95th percentile of the approved regimen.

The alternative initiation regimen has no impact on steady state maintenance concentration.

Subjects who are CYP2D6 Poor Metabolizers

Figure 6A:
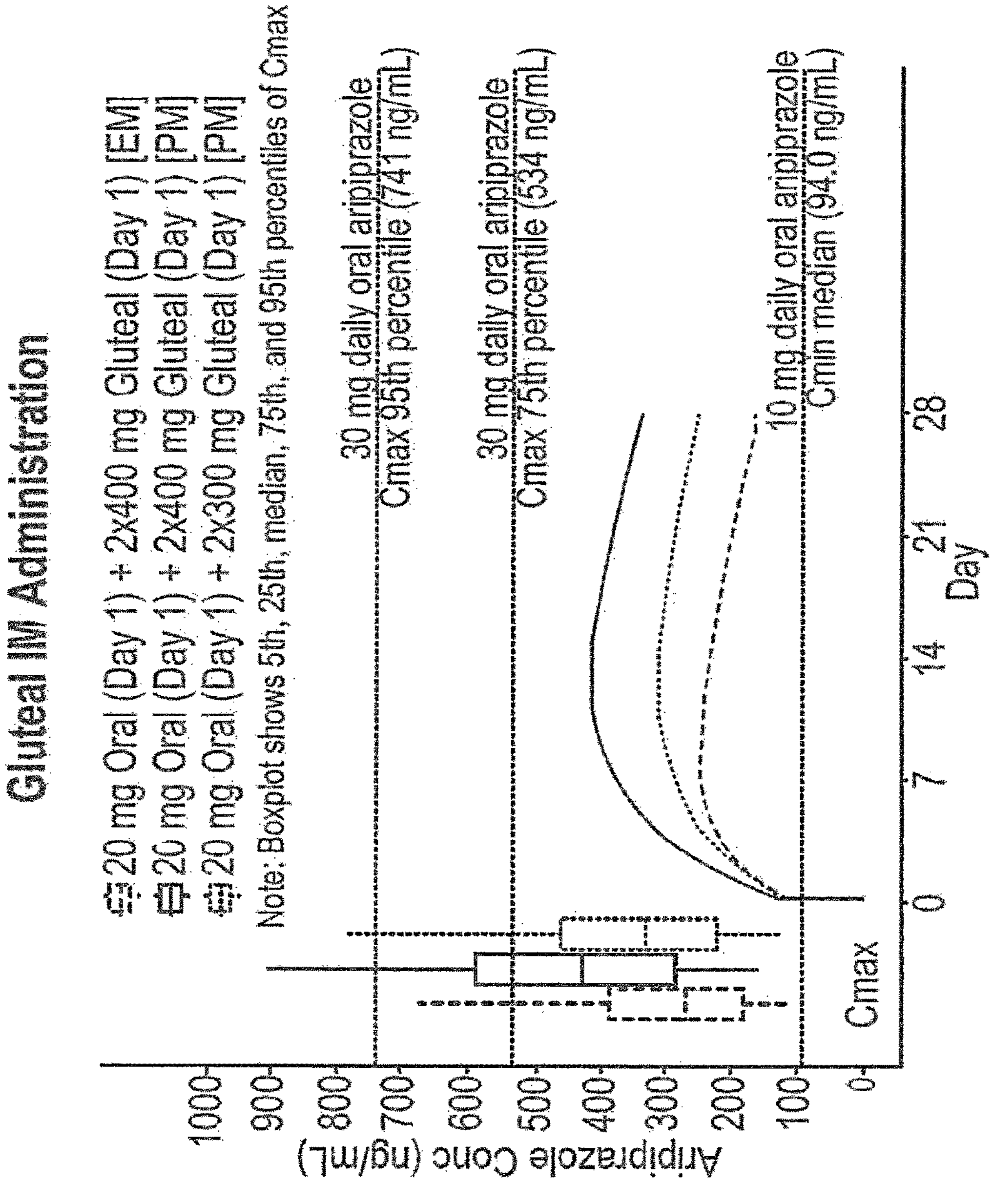
FIGS. 6A and 6B are diagrams of simulated median aripiprazole concentration time profiles boxplots of $C_{max}$ following Ability Maintena(R) initiation regimens to extensive and poor CYP2D6 metabolizers. The boxplot shows $5^{th}$, $25^{th}$, median, $75^{th}$, and $95^{th}$ percentiles of $C_{max}$.
Figure 6B:
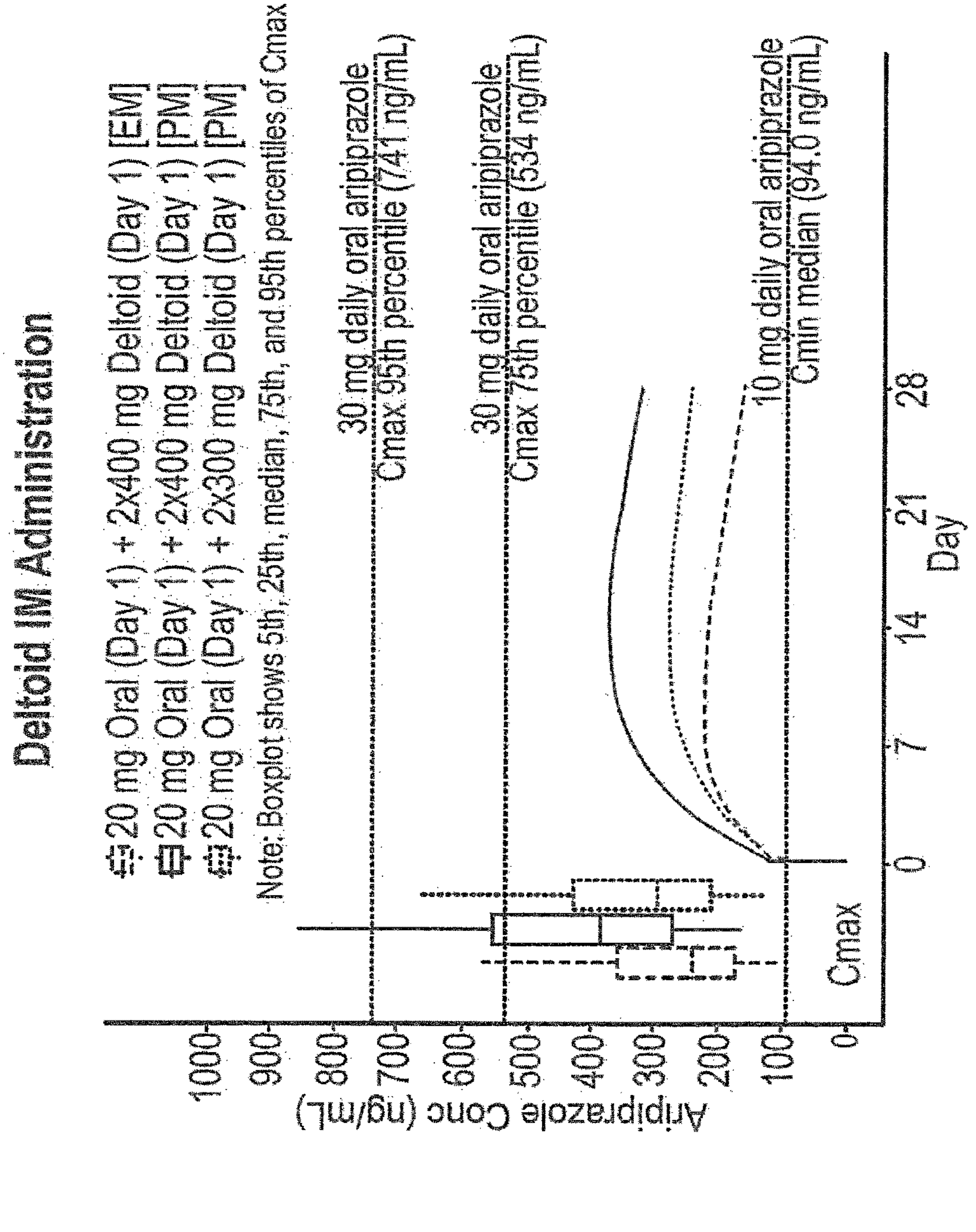

In subjects who are known to be cytochrome P450 2D6 poor metabolizers (CYP2D6 PM), the currently approved IM depot initiation dose should be reduced from 400 to 300 mg due to an approximately 50% lower apparent clearance of aripiprazole. Simulations were thus performed to predict aripiprazole concentrations following administration of the alternative initiation regimen to CYP2D6 extensive metabolizers (EM) and PM subjects. A comparison of the simulated median concentration time profiles and boxplots of maximum aripiprazole plasma concentrations (Cmax) following a single dose of 20 mg oral aripiprazole along with two administrations of either 400 mg (CYP2D6 EM and PM subjects) or 300 mg (only CYP2D6 PM subjects) Abilify Maintena(R) in the gluteal or deltoid sites is presented in FIGS. 6A and 6B. In FIGS. 6A and 6B, the approved initiation regimen was 10 to 20 mg oral (14 days) and 400 mg IM depot (Day 1).

Figure 7A:
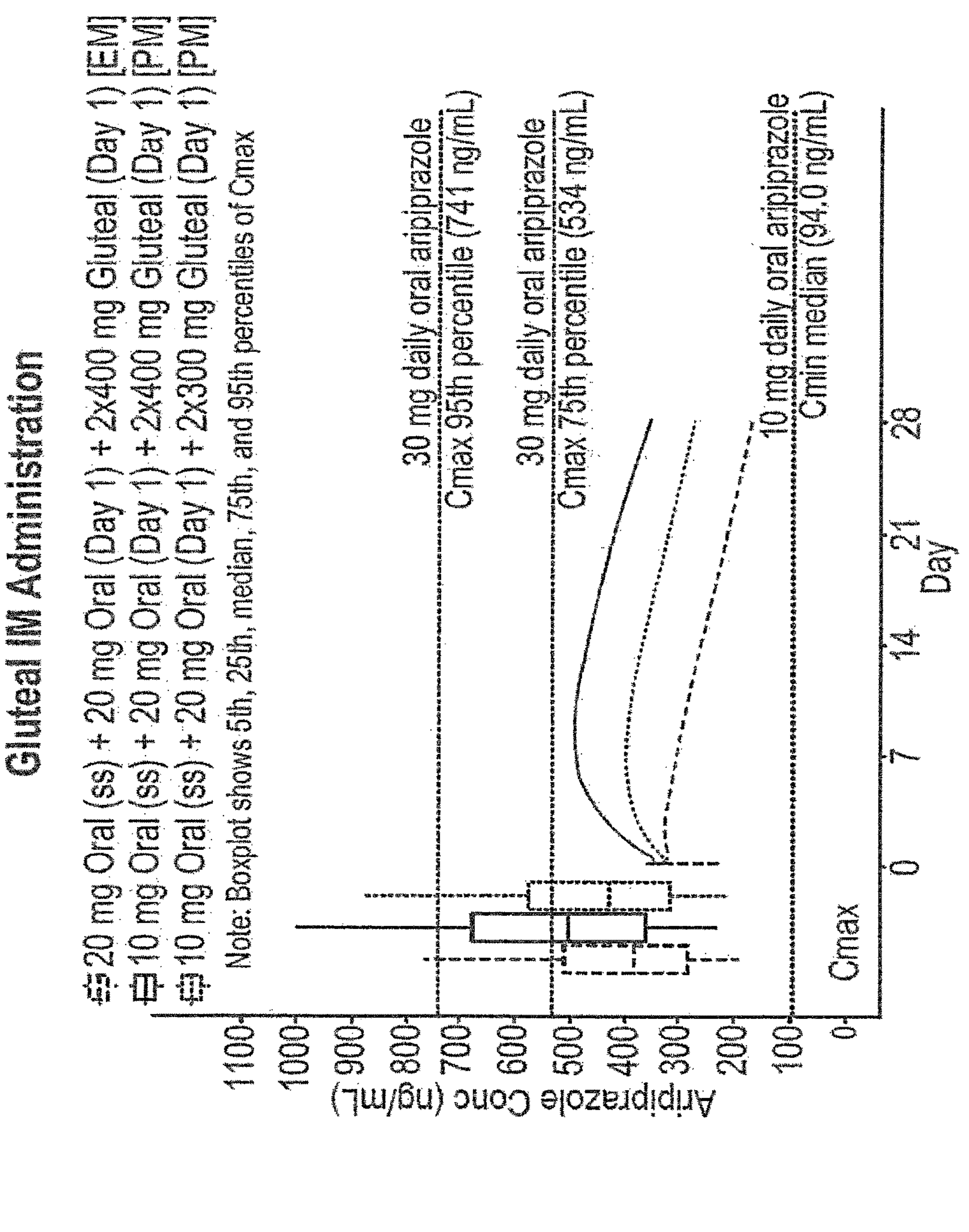
FIGS. 7A and 7B are diagrams of simulated median aripiprazole concentration time profiles and boxplots of $C_{max}$ following Ability Maintena(R) initiation regimens to extensive and poor metabolizers already stabilized on oral aripiprazole. The boxplot shows $5^{th}$, $25^{th}$, median, $75^{th}$, and $95^{th}$ percentiles of $C_{max}$.
Figure 7B:
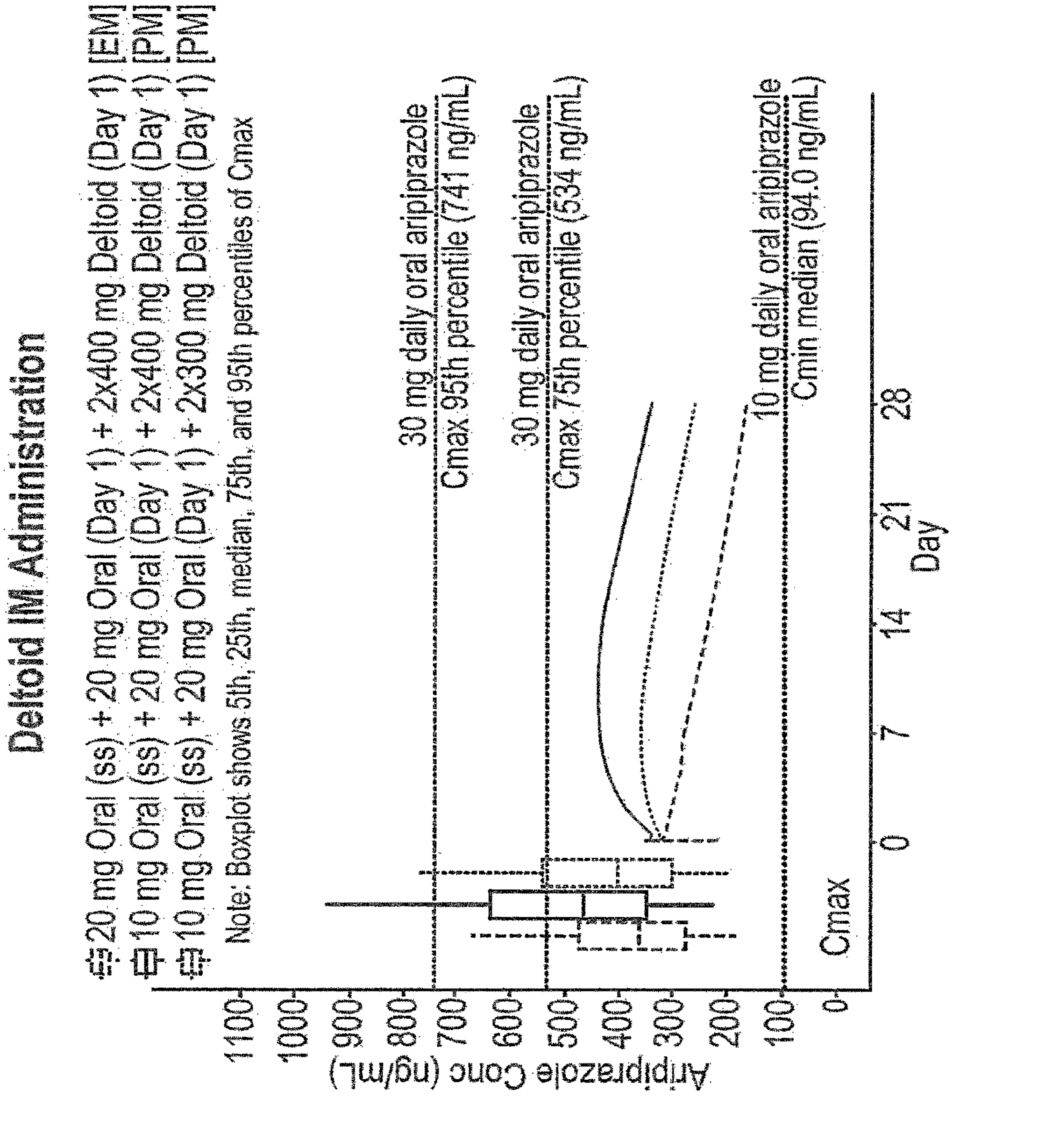
Figure 8A:
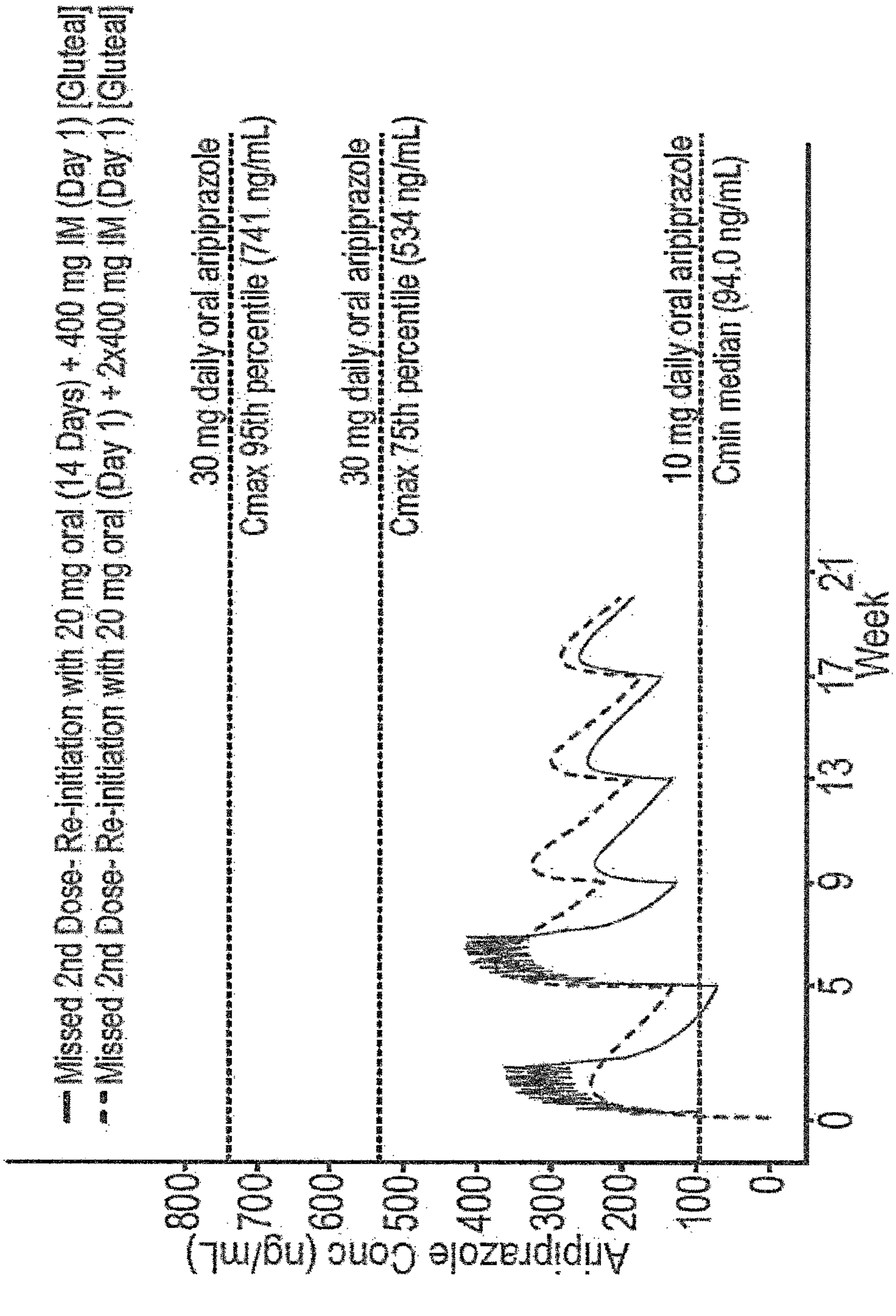
FIGS. 8A-8D are diagrams of simulated median pharmacokinetic profiles following initiation and re-initiation with current or alternative initiation regimen 5 weeks after the previous intramuscular depot dose.
Figure 8B:
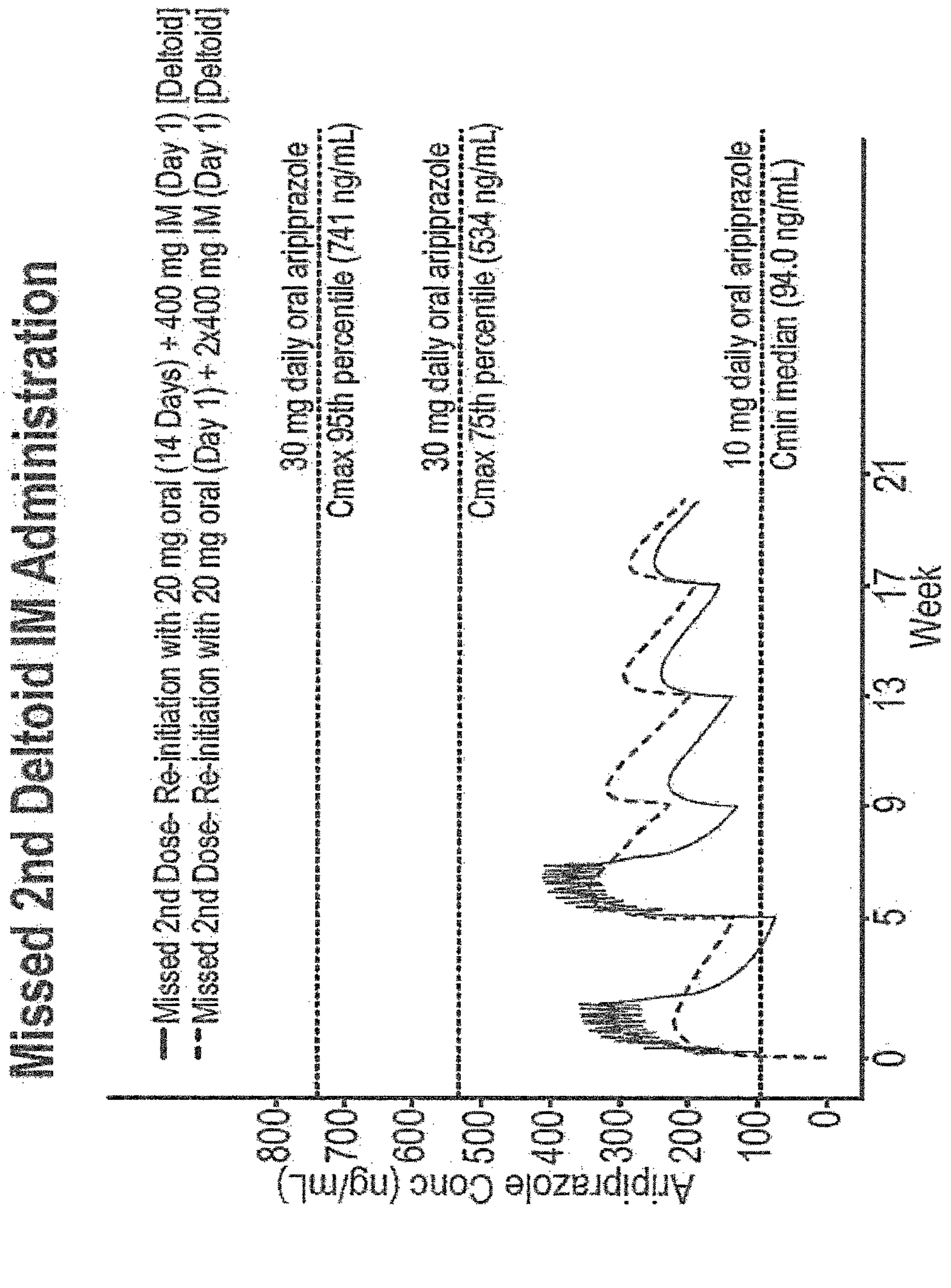
Figure 8C:
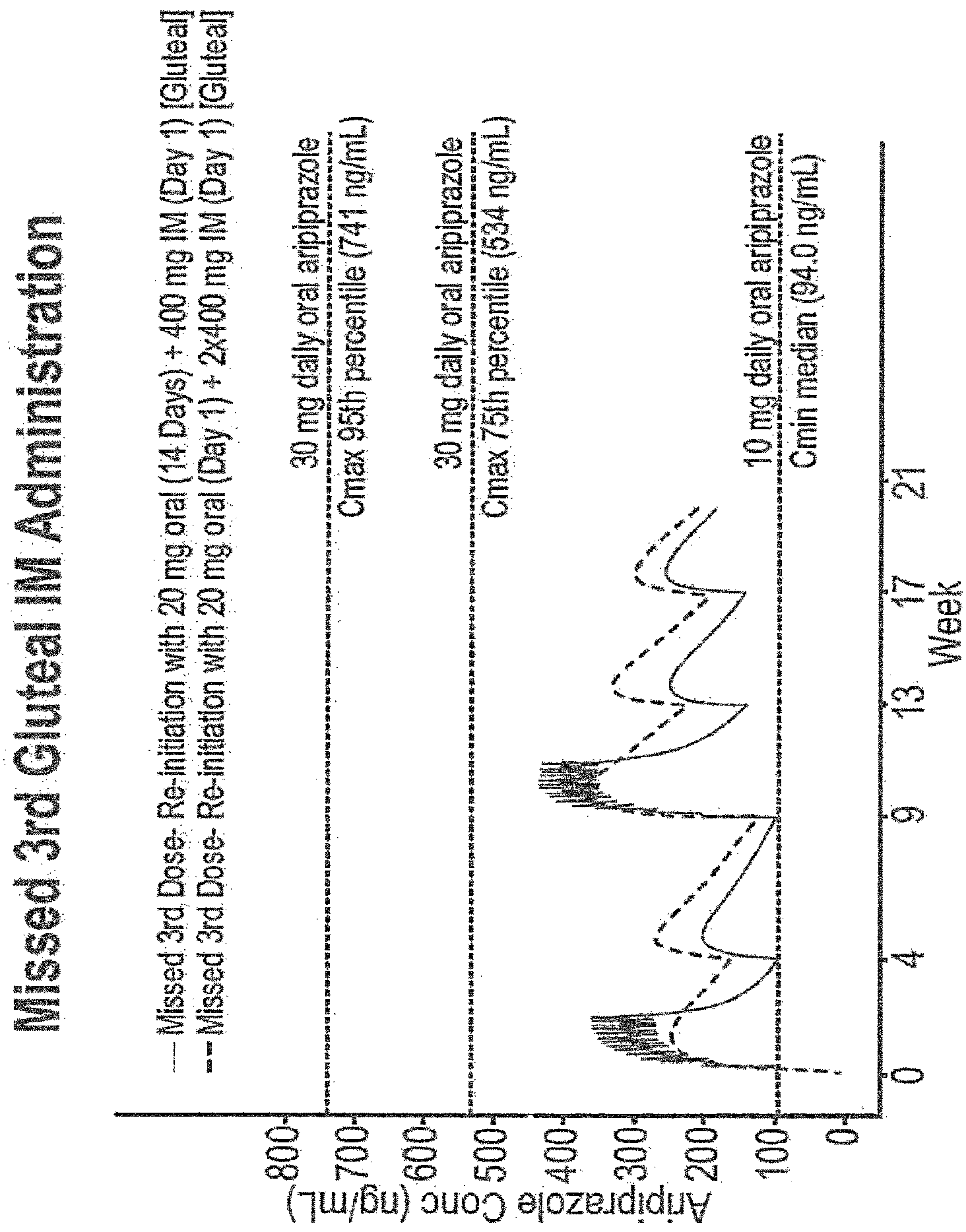
Figure 8D:
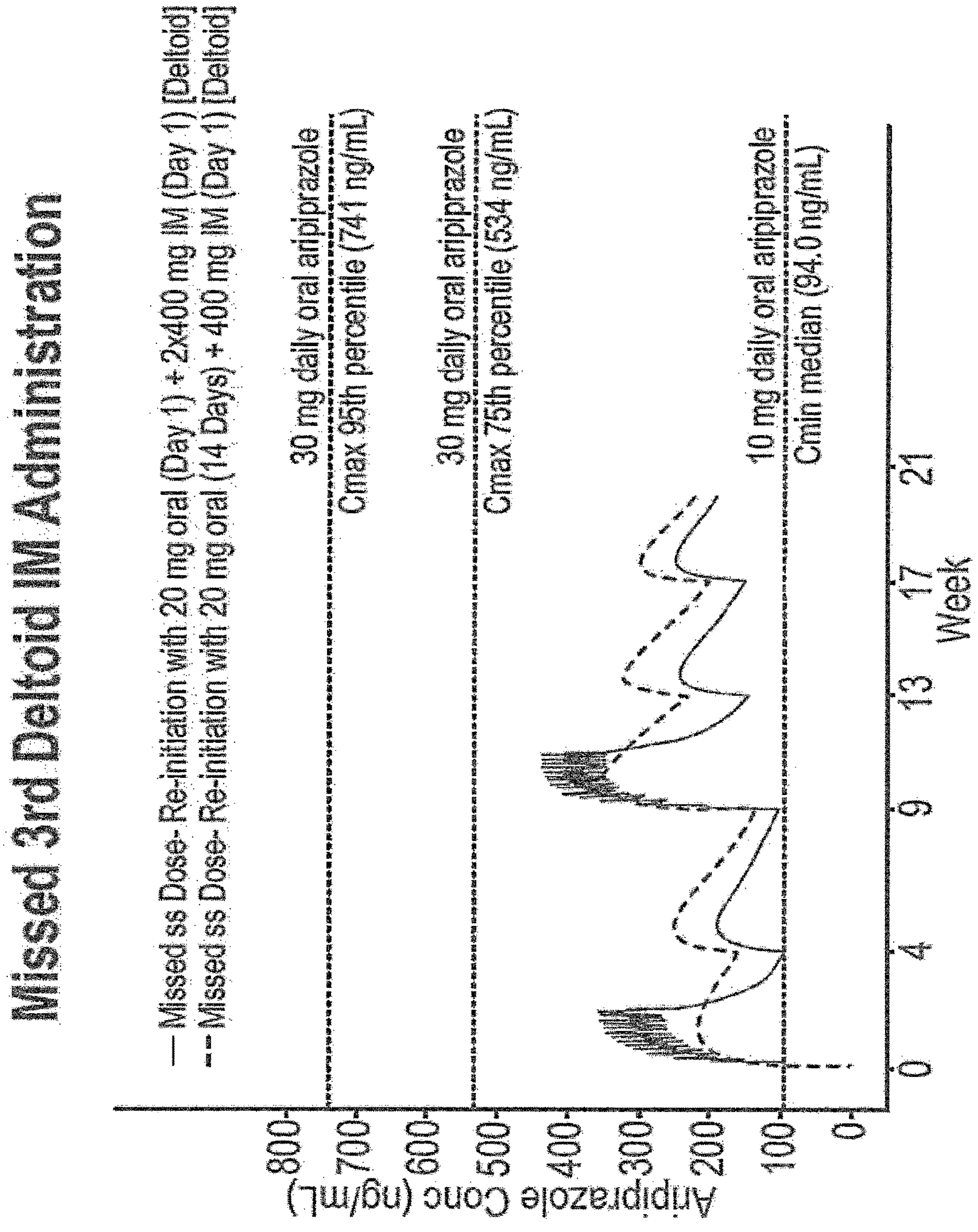
Figure 9A:
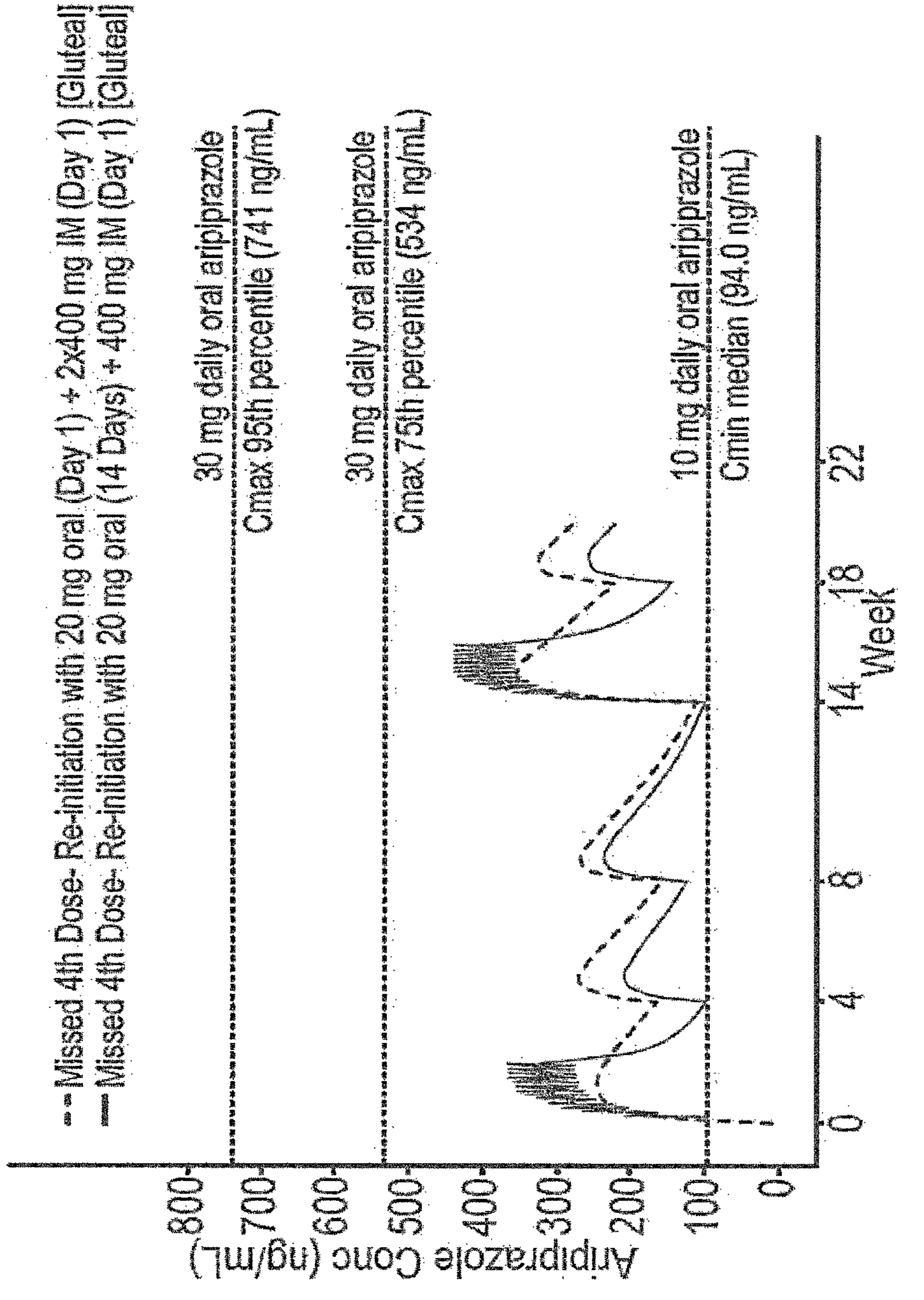
FIGS. 9A-9D are diagrams of simulated median pharmacokinetic profiles following initiation and re-initiation with the current or alternative initiation regimen 6 weeks after the previous intramuscular depot dose.
Figure 9B:
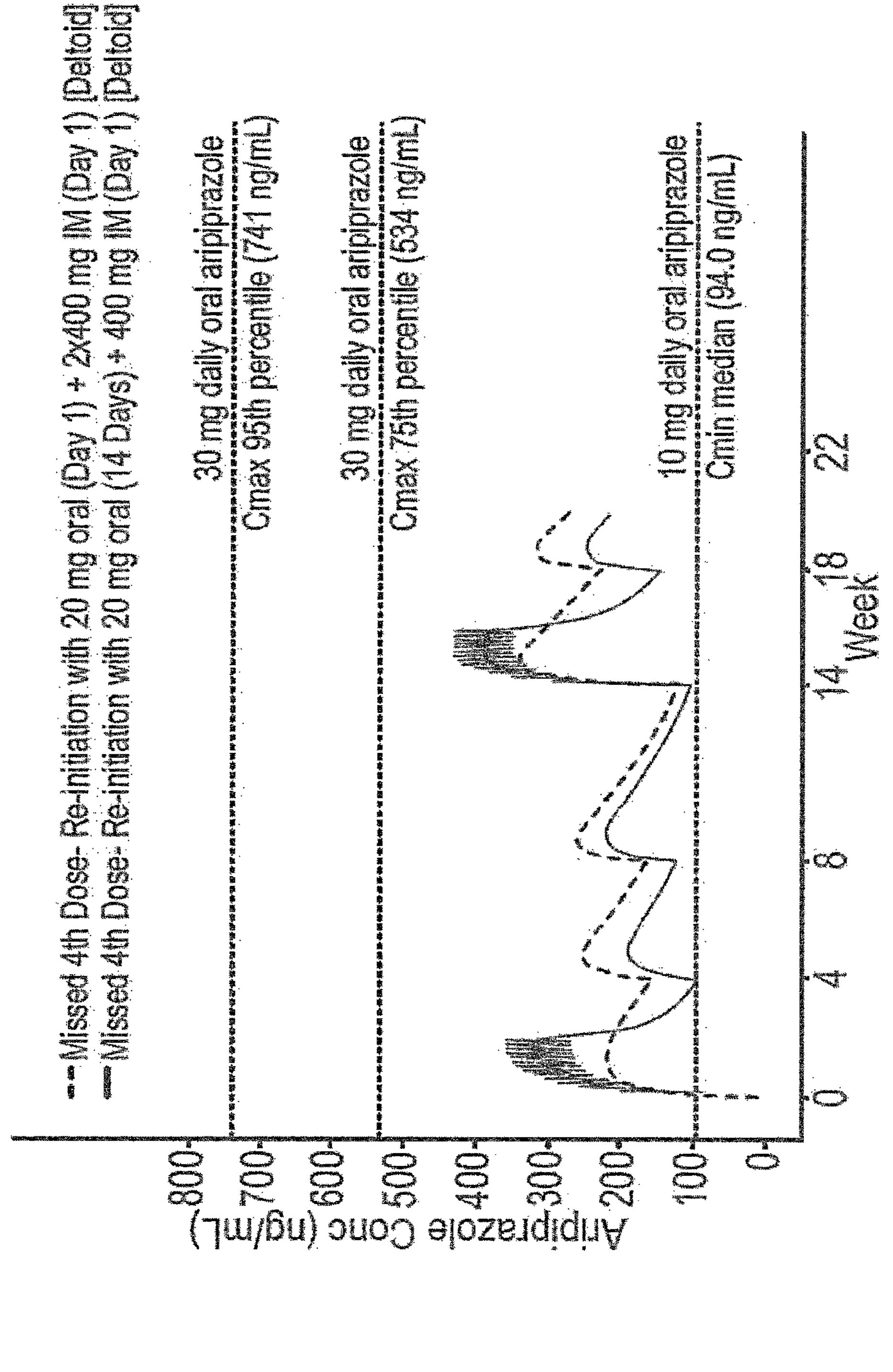
Figure 9C:
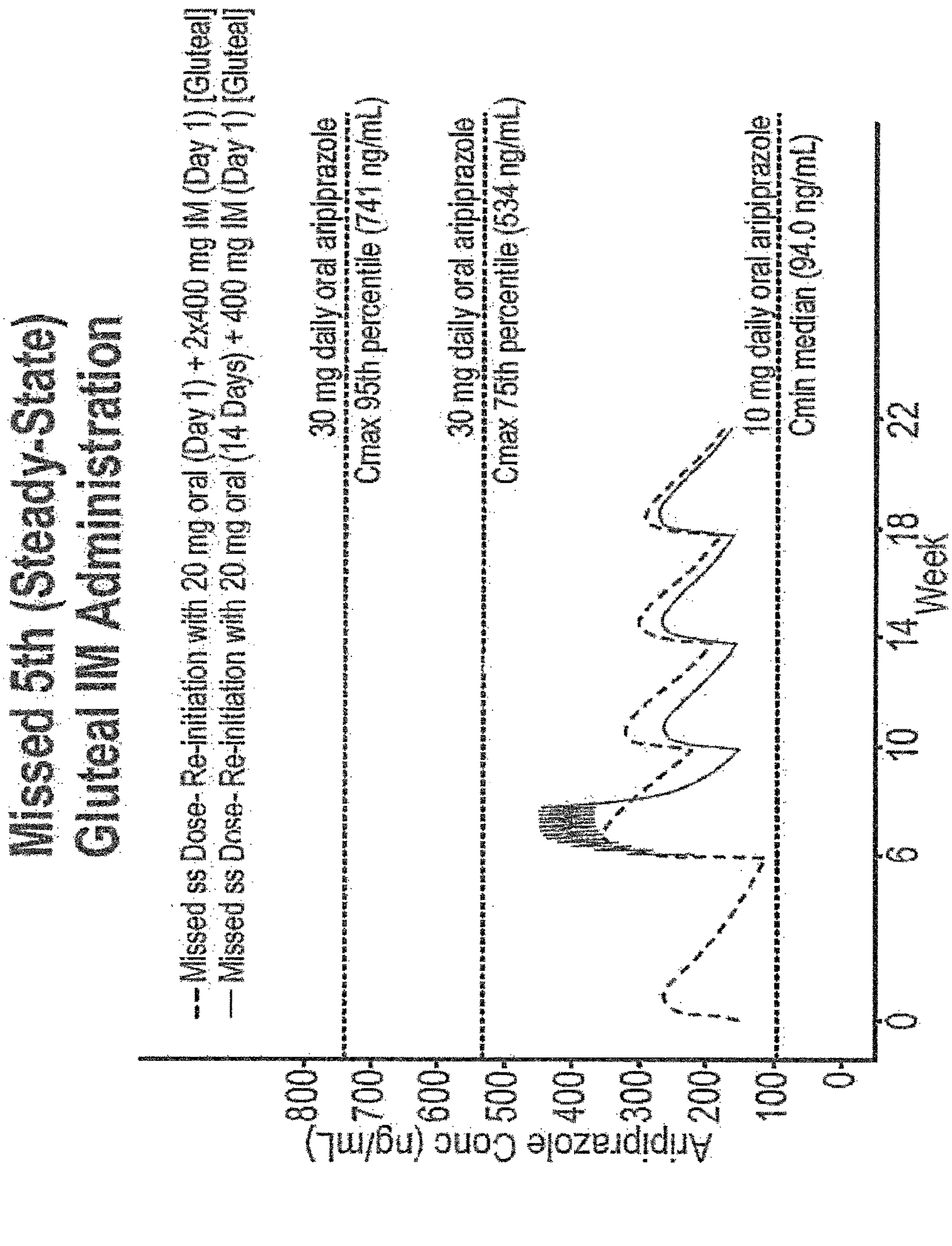
Figure 9D:
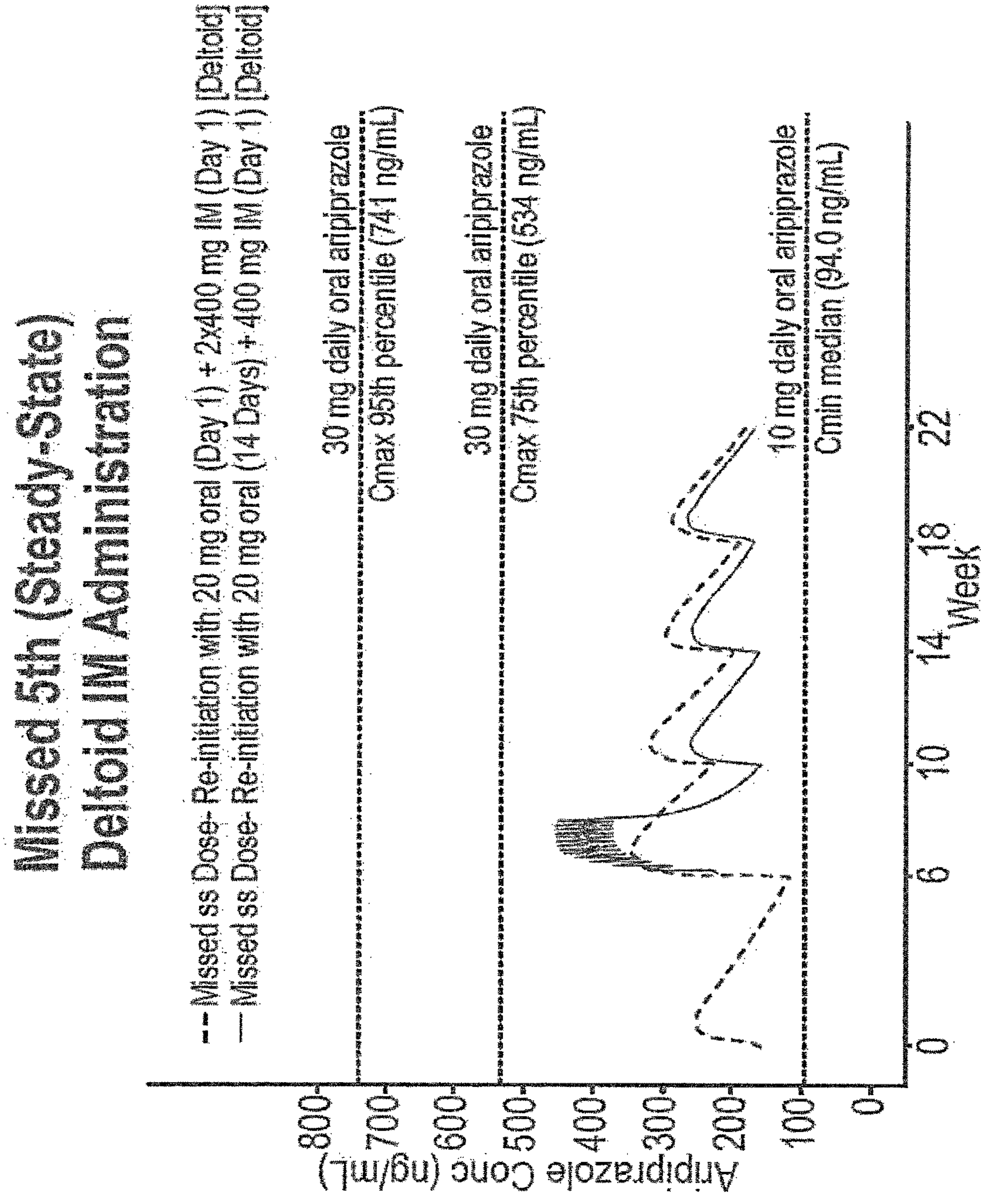

Simulations of plasma concentrations were performed to also allow comparison of the simulated median concentration time profiles and boxplots of aripiprazole Cmax following a single dose of 20 mg oral aripiprazole along with two administrations of cither 400 mg (CYP2D6 EM and PM subjects) or 300 mg (CYP2D6 PM subjects only) IM depot aripiprazole formulation in the gluteal or deltoid sites of subjects or patients with prior stabilization on 20 mg (EM) or 10 mg (PM) oral aripiprazole. These simulations are presented in FIGS. 7A and 7B. In FIGS. 7A and 7B, the approved initiation regimen is 10 to 20 mg oral (14 days)+400 mg IM depot (Day 1). The starting concentration at time zero is the average concentration at steady state for CYP2D6 EM stabilized on 20 mg oral aripiprazole and PM subjects stabilized on 10 mg oral aripiprazole. For PMs, prior oral dose was reduced by half (10 mg instead of 20 mg).

As expected, simulations resulted in CYP2D6 PM subjects exhibiting higher aripiprazole Cmax and exposure compared to CYP2D6 EM subjects when both receive two administrations of 400 mg IM depot aripiprazole formulation. Thus, a dose reduction of the proposed regimen from two 400 mg IM depot aripiprazole formulation administrations to two 300 mg IM depot aripiprazole formulation administrations along with a single dose of 20 mg oral aripiprazole is recommended for known CYP2D6 PM subjects or patients to ensure concentrations following the alternative initiation regimen are comparable to the currently approved regimen and remain within or slightly above the therapeutic window.

Missed Maintenance IM Depot Dose

Simulations were performed to assess aripiprazole concentrations following a missed second, third, fourth, or steady-state dose of IM depot aripiprazole formulation to determine whether the alternative initiation regimen could be applicable to situations when the currently approved initiation regimen requires concurrent oral administration of aripiprazole for 2 weeks with a single IM depot aripiprazole formulation injection.

A comparison of the simulated median aripiprazole plasma concentrations following administration of the alternative initiation regimen or the currently approved initiation regimen in the gluteal or deltoid site when the second or third IM depot aripiprazole formulation dose is administered 5 weeks after the previous injection are provided in FIGS. 8A-8D. In FIGS. 8A-8D, the approved initiation regimen was 10 to 20 mg oral (14 days) and 400 mg IM depot (Day 1).

A comparison of the simulated median aripiprazole plasma concentrations following administration of the alternative initiation regimen or the currently approved initiation regimen in the gluteal or deltoid site when the 4th or 5th (steady-state) dose is administered 6 weeks after the previous injection are provided in FIGS. 9A-9D. In FIGS. 9A-9D, the approved initiation regimen was 10 to 20 mg oral (14 days) and 400 mg IM depot (Day 1).

In all simulations, administration of the alternative initiation regimen following a missed maintenance IM depot resulted in median aripiprazole concentrations above the lower threshold of the therapeutic window and similar to those following the approved initiation regimen.

Based on the results of the simulations, the alternative initiation regimen may be administered in place of concomitant oral aripiprazole for 14 days together with a single IM depot formulation of aripiprazole injection on Day 1 when a maintenance IM depot dose is missed. Such a treatment strategy following a missed dose is consistent with that in the Abilify Maintena(R) label.

Comparison and Analyses of Results Across Trials

Figure 11:
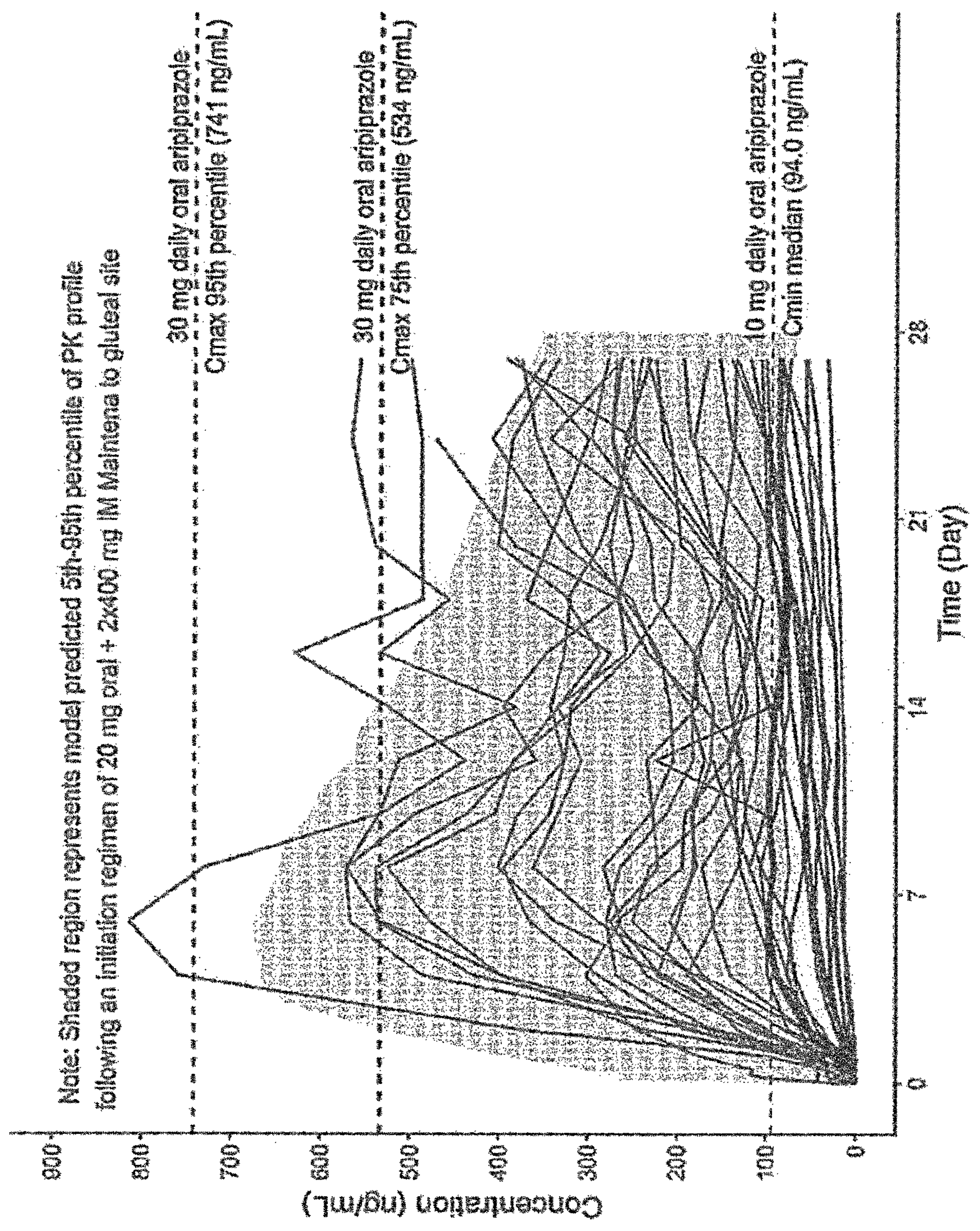
FIG. 11 is a diagram of composition aripiprazole plasma concentration time profiles following administration of a single dose of 780 mg (N=18) or 1200 mg (N=13) aripiprazole long acting injectable and mean plasma concentration following administration of a single dose of 400 mg Abilify Maintena(R) to the gluteal muscle of subjects with schizophrenia. The shaded region represents model predicted $5^{th}$-$95^{th}$ percentile of PK profile following an initiation regimen of 20 mg oral+2×400 mg IM Maintena(R) to gluteal site.

An analysis was performed to evaluate observed safety outcomes from a subset of 17 subjects from the phase I clinical trial describe below with plasma concentration time profiles that fall within the 5th to 95th percentile of simulated concentrations following administration of the alternative initiation regimen and are consistently above the mean PK profile following a single gluteal administration of 400 mg Abilify Maintena(R). A graphical comparison of all aripiprazole concentration time profiles following a single dose of 780 mg (N=18) or 1200 mg (N=13) aripiprazole LAI to the gluteal muscle (from a previous clinical trial), with aripiprazole concentration time profiles from the subset of 17 subjects highlighted in red, is presented in FIG. 11. In FIG. 11, the N equals the number of subjects; the subset of 17 subjects from a trial with plasma concentration time profiles that fall within the 5th to 95th percentile of simulated concentration following administration of the alternative initiation regimen and are consistently above the mean PK profile following a single gluteal administration of 400 mg Abilify Maintena(R); and lower limit of quantitation of aripiprazole was 0.500 ng/mL.

For reference, the mean (i.e., the lower dark horizontal line) aripiprazole plasma concentration time profile following administration of a single dose of 400 mg Abilify Maintena(R) to the gluteal muscle and the 5th to 95th percentile of simulated concentrations (final combined model) following administration of the alternative initiation regimen (20 mg oral [Day 1]+2×400 mg aripiprazole IM depot formulation [Day 1]) to the gluteal site (shaded area) are also presented.

Of the 17 subjects identified, 7 subjects were treated with 1200 mg aripiprazole LAI and 10 subjects were treated with 780 mg aripiprazole LAI. A review of the safety data from these subjects did not identify any unexpected AEs and it was concluded that their safety profile was in accordance with the known safety profile of Abilify Maintena(R).

CONCLUSIONS

Simulations indicated that the two-injection start regimen of two administrations of aripiprazole once-monthly at separate gluteal and/or deltoid injection sites with a single 20 mg dose of oral aripiprazole on the first day of treatment regimen would: (1) achieve therapeutic aripiprazole plasma concentrations on the first day of treatment; (2) support consistent clinical effectiveness over the entire dosing interval; (3) result in comparable aripiprazole plasma concentrations thus, safety profile, to the currently approved (traditional) initiation regimen; and (4) provide a new initiation option which obviates the need for the 14-day oral tablet supplementation, potentially reducing compliance related undertreatment during the initiation phase of treatment.

A Phase 1, Open Label, Single Ascending Dose, Parallel Arm Trial to Determine the Pharmacokinetics, Safety, and Tolerability of Aripiprazole 2 Month Intramuscular Depot Administered Gluteally in Adult Subjects with Schizophrenia This trial was an open-label, single ascending dose, parallel-arm, multiple-center trial to determine the PK, safety, and tolerability of single-dose administration of 780 mg (Cohort 1) and 1200 mg (Cohort 2) of a high dose formulation of aripiprazole LAI that is in the gluteal muscle of adult subjects with schizophrenia. Data from this trial is supportive information, as it was evaluated for instances in which aripiprazole plasma concentrations increased at a similar rate and reached levels predicted in simulations for the alternative initiation regimen. Overall, aripiprazole LAI was well tolerated when administered IM as a single dose of 780 mg and 1200 mg to adult subjects with schizophrenia. In a subset of 17 subjects, the administration of aripiprazole LAI resulted in higher aripiprazole plasma concentrations as well as faster absorption rates, resulting in aripiprazole plasma concentration time profiles that fell within the 5th to 95th percentile of simulated concentrations following administration of the proposed alternative initiation regimen and were consistently above the mean PK profile following a single gluteal administration of 400 mg Abilify Maintena (R) (FIG. 1). Safety data from this subset of subjects was evaluated and compared to the known safety profile of Abilify Maintena(R). Further details of this analysis are provided under the section entitled "Comparison and Analyses of Results Across Trials."

Figure 12:
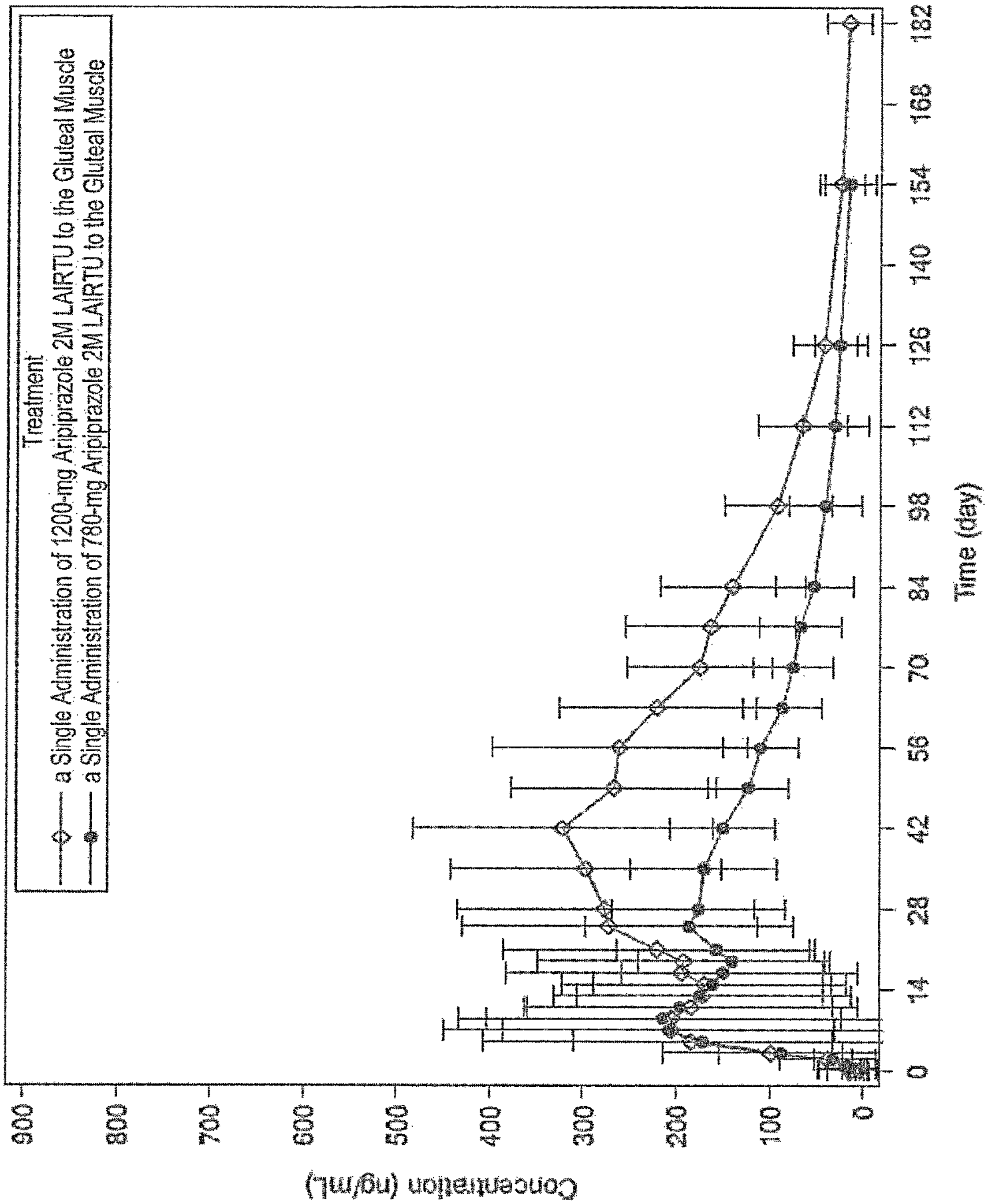
FIG. 12 diagrams mean (SD) aripiprazole plasma concentration time profiles following administration of a single dose of 780 mg (N=18) or 1200 mg (N=13) aripiprazole 2M long acting injectable ready to use to the gluteal muscle of subjects with schizophrenia.

The aripiprazole LAI was an extended release presentation for dosing every 2 months at the dose levels evaluated. The extension of the dosing interval for the aripiprazole LAI was primarily through an increase in the dose while maintaining minimum aripiprazole concentrations that are comparable to Abilify Maintena(R) after multiple doses. The aripiprazole LAI was engineered with higher aripiprazole concentrations in the drug product (300 mg/mL vs 200 mg/mL) and minor changes to the vehicle compared to currently marketed/approved Abilify Maintena(R). The mean aripiprazole particle size distribution and the dissolution profile for the aripiprazole LAI formulation were comparable with the Abilify Maintena(R) formulation and the formulation was expected to have a similar extended release profile compared with the approved Abilify Maintena(R) formulation. Mean (standard deviation [SD]) aripiprazole plasma concentration time profiles following administration of a single dose of 780 mg or 1200 mg aripiprazole to the gluteal muscle in subjects with schizophrenia are presented in FIG. 12.

A summary of the aripiprazole PK parameters following single-dose administration of a single dose of 780 mg or 1200 mg aripiprazole to the gluteal muscle in subjects with schizophrenia is presented in Table 2 below.

TABLE 2

Mean (SD) Aripiprazole Pharmacokinetic Parameters Following Administration of a Single Dose of 780 mg or 1200 mg Aripiprazole Long Acting Injectable to the Gulteal Muscle of Subjects with Schizophrenia

| PK Parameter | Aripiprazole 2M RTU LAI 780 mg (N = 18) | Aripiprazole 2M RTU LAI 1200 mg (N = 13) |
|---|---|---|
| Cmax (ng/mL) | 271 (157) | 391 (200) |
| tmax(day)[a] | 25.1 (4.07-76.0) | 41.0 (6.09-61.9) |
| AUCt (ng · day/mL) | 12600 (3710) | 23800 (7620) |
| AUC∞ (ng · day/mL) | 13400 (4600)[b] | 24700 (8080)[c] |
| t½ (day) | 22.1 (16.5)[b] | 20.0 (9.2)[c] |
| CL/F (mL/day/kg) | 763 (299)[b] | 596 (207)[c] |
| Cmax/Dose (ng/mL/mg) | 0.347 (0.201) | 0.326 (0.167) |
| AUCt/Dose ([ng · day/mL]/mg) | 16.1 (4.75) | 19.8 (6.35) |
| AUC∞/Dose([ng · day/mL]/mg) | 17.2 (5.90)[b] | 20.6 (6.73)[c] |

From Table 2, it is noted that AUC∞ is area under the concentration-time curve calculated from time zero to infinity; AUCt is area under the concentration-time curve calculated to the last observable concentration at time t; CL/F is apparent clearance of drug from plasma after extravascular administration; RTU is ready to use; tmax is time to maximum (peak) plasma concentration; t1/2 is elimination half-life. Additionally, a Median (minimum-maximum); $^{b}$n=14; and $^{c}$n=11.

Conclusions from this data include, for example:

- Aripiprazole LAI was well tolerated when administered IM as a single dose of 780 and 1200 mg to adult subjects with schizophrenia.
- Single-dose administration of 780 or 1200 mg aripiprazole LAI to the gluteal muscle resulted in, respectively, a 100% and 200% increase in aripiprazole Cmax and exposure (area under the concentration-time curve [AUC] calculated from time zero to infinity [AUC∞] and AUC calculated to the last observable concentration at time t [AUCt]) than previously observed following single-dose administration of 400 mg Abilify Maintena(R) to the gluteal muscle.
- Single-dose administration of 780 or 1200 mg aripiprazole LAI to the gluteal muscle resulted in a slightly less than proportional increase in aripiprazole Cmax and a slightly more than dose proportional increase in exposure (AUCt and AUC∞) based on mean values corrected for dose.
- Administration of 780 mg aripiprazole LAI to the gluteal muscle resulted in shorter median time to maximum (peak) plasma concentration (tmax) values for aripiprazole (25.1 days vs 41.0 days) when compared to the 1200 mg dose.
- Following administration of 780 or 1200 mg aripiprazole LAI to the gluteal muscle, mean terminal elimination half-life (t1/2) values for aripiprazole (22.1 and 20.0 days, respectively) were comparable, and similar to the median t1/2 following single-dose administration of 400 mg Abilify Maintena(R) to the gluteal muscle (24.0 days).
- A consistent increase in aripiprazole concentrations followed by a decline and a secondary peak in concentrations were observed following administration of 780 or 1200 mg aripiprazole LAI to the gluteal muscle based on examination of mean, median, and individual concentration-time profiles.
- Additionally, this Phase I trial supports the use of the present disclosure of a method of dose initiation for an aripiprazole treatment to a patient in need thereof comprising: administering two, separate injections of an aripiprazole intramuscular (IM) depot formulation ranging from about 10 mg to about 500 mg of aripiprazole to the patient at separate gluteal and/or deltoid injection sites, and a single dose of oral aripiprazole, wherein administration occurs on a first day of the treatment. That is, the use of two injections ranging from about 10 mg to about 500 mg of aripiprazole did not result in any unexpected AEs and the safety profile was in accordance with the known safety profile of Ability Maintena(R).

All publications and patents mentioned herein are hereby incorporated by reference in their entirety as if each individual publication or patent was specifically and individually indicated to be incorporated by reference.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub range within the stated ranges in different embodiments of the disclosure, to the tenth of the unit of the lower limit of the range, unless the context clearly dictates otherwise.

Those of ordinary skill in the art will recognize or be able to ascertain using no more than routine experimentation, many equivalents to the specific embodiments of the disclosure described herein. Such equivalents are intended to be encompassed by the following claims.

The invention claimed is:

1. A method of administering an aripiprazole treatment to a patient in need thereof comprising:

administering a one-day dose initiation consisting of two, separate injections of an aripiprazole intramuscular (IM) depot formulation, wherein each injection comprises 300 mg or 400 mg of aripiprazole, to the patient at separate injection sites chosen from gluteal sites, deltoid sites, and a gluteal site and a deltoid site, and a single dose of oral aripiprazole ranging from about 10 mg to about 30 mg of aripiprazole in a tablet, wherein the step of administering the two separate injections and the single oral dose occurs on a first day of the treatment, wherein the patient has schizophrenia, and wherein the aripiprazole intramuscular (IM) depot formulation comprises aripiprazole monohydrate.

2. The method according to claim 1, wherein each of the two, separate injections comprise 400 mg of aripiprazole.

3. The method according to claim 1, wherein each of the two, separate injections comprise 300 mg of aripiprazole.

4. The method according to claim 1, further comprising after the first day of treatment, administering a single monthly, maintenance injection of the aripiprazole IM depot formulation comprising 400 mg of aripiprazole.

5. The method according to claim 1, further comprising after the first day of treatment, administering a single monthly, maintenance injection of the aripiprazole IM depot formulation comprising 300 mg of aripiprazole.

6. The method according to claim 1, further comprising after the first day of treatment, administering a single monthly, maintenance injection wherein each maintenance injection is administered no sooner than 26 days after the previous injection.

7. The method according to claim 1, wherein the two, separate injections of the aripiprazole IM depot formulation are administered at separate gluteal and/or deltoid injection sites of the patient.

8. The method according to claim 1, wherein the two, separate injections of the aripiprazole IM depot formulation are administered at separate gluteal injection sites of the patient.

9. The method according to claim 1, wherein the single dose of oral aripiprazole is 20 mg.

10. The method according to claim 1, wherein the single dose of oral aripiprazole is 10 mg.

* * * * *